(12) United States Patent
Kim et al.

(10) Patent No.: US 6,894,075 B2
(45) Date of Patent: May 17, 2005

(54) 4'-DEMETHYL-4'-O-SUBSTITUTED-1-DEOXYPODOPHYLLOTOXIN DERIVATIVE AND GEOMETRIC ISOMER THEREOF, PROCESS FOR THE PREPARATION THEREOF AND ANTI-CANCER COMPOSITION COMPRISING THE SAME

(75) Inventors: Song-Bae Kim, 533-2, Banggok-ri, Banpo-myun, Gongju-shi, 314-920, Choongchungnam-do (KR); Byung-Zun Ahn, Taejeon (KR); Yong Kim, Taejeon (KR); Young-Jae You, Choongchungnam-do (KR)

(73) Assignee: Song-Bae Kim, Choongchungnam-do (KR)

( * ) Notice: Subject to any disclaimer, the term of this patent is extended or adjusted under 35 U.S.C. 154(b) by 33 days.

(21) Appl. No.: 10/415,366

(22) PCT Filed: Nov. 19, 2001

(86) PCT No.: PCT/KR01/01972

§ 371 (c)(1),
(2), (4) Date: Apr. 28, 2003

(87) PCT Pub. No.: WO02/40489

PCT Pub. Date: May 23, 2002

(65) Prior Publication Data

US 2004/0044058 A1 Mar. 4, 2004

(30) Foreign Application Priority Data

Nov. 20, 2000 (KR) ........................................ 2000-69004
Jul. 9, 2001 (KR) ........................................ 2001-40806

(51) Int. Cl.$^7$ ...................... A61K 31/335; A61K 31/34
(52) U.S. Cl. ........................ 514/463; 514/468; 549/298
(58) Field of Search ........................ 549/298; 514/463, 514/468

(56) References Cited

FOREIGN PATENT DOCUMENTS

EP           778282 A1    12/1996
WO     WO 99/18109 A1     4/1999

OTHER PUBLICATIONS

Gordaliza, J. Med. Chem, 1996, vol. 39, pp. 2865–2868.

Primary Examiner—Amelia A. Owens
(74) Attorney, Agent, or Firm—Birch, Stewart, Kolasch & Birch, LLP

(57) ABSTRACT

The present invention provides a novel 4'-demethyl-4'-O-substituted-1-deoxypodophyllotoxin derivative, a geometric isomer thereof, a process for the preparation thereof, and an anticancer composition comprising the same.

6 Claims, No Drawings

4'-DEMETHYL-4'-O-SUBSTITUTED-1-DEOXYPODOPHYLLOTOXIN DERIVATIVE AND GEOMETRIC ISOMER THEREOF, PROCESS FOR THE PREPARATION THEREOF AND ANTI-CANCER COMPOSITION COMPRISING THE SAME

This application is the national phase under 35 U.S.C. § 371 of PCT International Application No. PCT/KR01/01972 which has an International filing date of Nov. 19, 2001, which designated the United States of America.

TECHNICAL FIELD

The present invention relates to a novel 4'-demethyl-4'-O-substituted-1-deoxypodophyllotoxin derivative represented by the following formula (1):

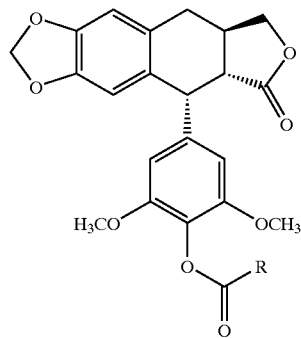

(1)

in which
R represents -A-$NH_2$; —NH—$R^1$; phenyl-$C_{2-4}$alkenyl unsubstituted or substituted by 1 to 5 $C_{1-4}$alkoxy; benzyl unsubstituted or substituted by amino or di$C_{1-4}$ alkylamino; straight-chain or branched $C_{1-21}$alkyl, $C_{15-21}$ alkenyl, $C_{15-21}$alkadienyl, $C_{15-21}$alkatrienyl, $C_{15-21}$ alkatetraenyl, or $C_{15-21}$alkahexaenyl; retinyl; or $C_{5-15}$carboxyalkyl,
wherein
A represents amino acid residue, —$(CH_2)_{n1}$—; or —$(CH_2)_{n2}$—$C_6H_5$,
n1 denotes an integer of 2 to 8,
n2 denotes an integer of 1 to 4, and
$R^1$ represents straight-chain or branched $C_{1-4}$alkyl unsubstituted or substituted by substituent(s) selected from a group consisting of halogen and hydroxy; cycloalkyl; haloacetyl; allyl; phenyl unsubstituted or substituted by substituent(s) selected from a group consisting of halogen, $C_{1-4}$alkoxy, $C_{1-4}$alkyl and $C_{1-4}$alkylthio; benzyl; benzoyl; or benzenesulfonyl, a geometric isomer thereof, to a process for the preparation thereof, and to an anticancer composition comprising the same.

BACKGROUND ART

Deoxypodophyllotoxin (DPT) is a kind of lignan compound isolated from nature as like podophyllotoxin. It has been reported that podophyllotoxin shows a cytotoxicity to some kinds of cancer cells. Etoposide, a derivative of podophyllotoxin, is now widely used for clinical purposes [see, I. Jardine; In Anticancer Agents based on Natural Product Models; J. M. Cassidy et al.; Eds.; Academic Press: New York, 319–351, 1980], and is known to show a special effect against SCLC (Small Cell Lung Cancer), malignant lymphoma, etc. [see, T. Utsugi et al.; cancer research, 56, 2809, 1996].

However, differently from podophyllotoxin, researches for deoxypodophyllotoxin (DPT) and derivatives thereof as an anticancer agent have not been carried out yet. Anticancer researches for this compound still remain at the step of cytotoxicity. San Feliciano et al., Planta Medica 59, 247, 1993; Arch. Pharm. 327, 175, 1994; D. B. M. Wickramaratne et al., Planta Medica, 61, 80, 1995; J. J. Chen et al., Planta Medica 62, 528, 1996; and M. Novelo et al., J. Nat. Pro. 56(10), 1728, 1993 reported that this compound shows a potent cytotoxicity against tumor cells, and R. S. Gupta et al., Cancer Research 43, 505–512, 1983; and J. D. Loike et al., Cancer Research 38, 2688–2693, 1978 reported that the cytotoxicity causes an inhibition of cell division through an inhibition of microtubule assembly (IC50; 0.6 mM). Further, T. Terada et al., Chem. Pharm. Bull., 40, 2720–2727, 1992 reported that mouse leukemia cell line L1210 was transplanted into CDF1 mouse, and in that case deoxypodophyllotoxin exhibited an extension effect of life span in about 12% compared with the negative control.

After the above reports, no more researches for the anticancer activity of deoxypodophyllotoxin derivatives have been carried out. This seems to be because deoxypodophyllotoxin does not show any anticancer activity in animal models due to its low bioavailability.

DISCLOSURE OF INVENTION

Thus, the present inventors prepared various deoxypodophyllotoxin derivatives and studied their anticancer activities in order to solve the above-mentioned problems. As a result, we identified that the compounds according to the present invention have a better biocompatibility and water solubility, and therefore exhibit a more potent anticancer activity than the existing deoxypodophyllotoxin, and then completed the present invention.

The present invention relates to a novel 4'-demethyl-4'-O-substituted-1-deoxypodophyllotoxin derivative of the following formula (1), a geometric isomer thereof, to a process for the preparation thereof, and to an anticancer composition comprising the same.

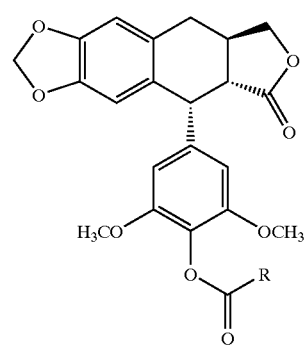

(1)

in which
R represents -A-$NH_2$; —NH—$R^1$; phenyl-$C_{2-4}$alkenyl unsubstituted or substituted by 1 to 5 $C_{1-4}$alkoxy; benzyl unsubstituted or substituted by amino or di$C_{1-4}$ alkylamino; straight-chain or branched $C_{1-21}$alkyl, $C_{15-21}$ alkenyl, $C_{15-21}$alkadienyl, $C_{15-21}$alkatrienyl, $C_{15-21}$ alkatetraenyl, or $C_{15-21}$alkahexaenyl; retinyl; or $C_{5-15}$carboxyalkyl,
wherein
A represents amino acid residue, —$(CH_2)_{n1}$—; or —$(CH_2)_{n2}$—$C_6H_5$,
n1 denotes an integer of 2 to 8, n2 denotes an integer of 1 to 4, and R¹ represents straight-chain or branched $C_{1-4}$alkyl unsubstituted or substituted by substituent(s) selected from a group consisting of halogen and hydroxy; cycloalkyl; haloacetyl; allyl; phenyl unsubstituted or substituted by substituent(s) selected from a group consisting of halogen, $C_{1-4}$alkoxy, $C_{1-4}$alkyl and $C_{1-4}$alkylthio; benzyl; benzoyl; or benzenesulfonyl.

Therefore, an object of the present invention is to provide a novel 4'-demethyl-4'-O-substituted-1-deoxypodophyllotoxin derivative of formula (1) above and a geometric isomer thereof.

It is another object of the present invention to provide a process for preparing the compound of formula (1) and a geometric isomer thereof.

It is still another object of the present invention to provide an anticancer composition comprising as an active ingredient the compound of formula (1) or the geometric isomer thereof together with pharmaceutically acceptable carriers.

BEST MODE FOR CARRYING OUT THE INVENTION

In the compound of formula (1) wherein R represents such a radical containing double bond(s) as alkenyl, alkadienyl, alkatrienyl, alkatetraenyl, each of the double bonds may exist in the form of cis or trans. Therefore, the present invention includes in its scope a geometric isomer of the compound of formula (1).

In the definition of the substituent A, the "amino acid residue" means a part of amino acid where —COOH group and —NH₂ group are excluded. Residues of alanine, leucine, valine, glycine, serine, methionine, phenylalanine, threonine and tyrosine are preferred.

Typical examples of the compound of formula (1) according to the present invention are as follows:
4'-demethyl-4'-O-alanoyl-1-deoxypodophyllotoxin;
4'-demethyl-4'-O-leucinoyl-1-deoxypodophyllotoxin;
4'-demethyl-4'-O-valinoyl-1-deoxypodophyllotoxin;
4'-demethyl-4'-O-glycinoyl-1-deoxypodophyllotoxin;
4'-demethyl-4'-O-serinoyl-1-deoxypodophyllotoxin;
4'-demethyl-4'-O-methionoyl-1-deoxypodophyllotoxin;
4'-demethyl-4'-O-phenylalanoyl-1-deoxypodophyllotoxin;
4'-demethyl-4'-O-threonoyl-1-deoxypodophyllotoxin;
4'-demethyl-4'-O-tyrosinoyl-1-deoxypodophyllotoxin;
4'-demethyl-4'-O-(3-aminopropanoyl)-1-deoxypodophyllotoxin;
4'-demethyl-4'-O-(4-aminobutanoyl)-1-deoxypodophyllotoxin;
4'-demethyl-4'-O-(5-aminopentanoyl)-1-deoxypodophyllotoxin;
4'-demethyl-4'-O-(6-aminohexanoyl)-1-deoxypodophyllotoxin;
4'-demethyl-4'-O-(7-aminoheptanoyl)-1-deoxypodophyllotoxin;
4'-demethyl-4'-O-(8-aminooctanoyl)-1-deoxypodophyllotoxin;
4'-demethyl-4'-O-(4-aminophenylacetyl)-1-deoxypodophyllotoxin;
4'-demethyl-4'-O-ethylcarbamoyl-1-deoxypodophyllotoxin;
4'-demethyl-4'-O-isopropylcarbamoyl-1-deoxypodophyllotoxin;
4'-demethyl-4'-O-(2-chloroethylcarbamoyl)-1-deoxypodophyllotoxin;
4'-demethyl-4'-O-cyclohexylcarbamoyl-1-deoxypodophyllotoxin;
4'-demethyl-4'-O-(2-hydroxyethyl)carbamoyl-1-deoxypodophyllotoxin;
4'-demethyl-4'-O-chloroacetylcarbamoyl-1-deoxypodophyllotoxin;
4'-demethyl-4'-O-allylcarbamoyl-1-deoxypodophyllotoxin;
4'-demethyl-4'-O-phenylcarbamoyl-1-deoxypodophyllotoxin;
4'-demethyl-4'-O-(4-fluorophenylcarbamoyl)-1-deoxypodophyllotoxin;
4'-demethyl-4'-O-(4-methoxyphenylcarbamoyl)-1-deoxypodophyllotoxin;
4'-demethyl-4'-O-(4-methylphenylcarbamoyl)-1-deoxypodophyllotoxin;
4'-demethyl-4'-O-(4-methylthiophenylcarbamoyl)-1-deoxypodophyllotoxin;
4'-demethyl-4'-O-(2-methoxyphenylcarbamoyl)-1-deoxypodophyllotoxin;
4'-demethyl-4'-O-benzylcarbamoyl-1-deoxypodophyllotoxin;
4'-demethyl-4'-O-benzoylcarbamoyl-1-deoxypodophyllotoxin;
4'-demethyl-4'-O-benzenesulfonylcarbamoyl-1-deoxypodophyllotoxin;
4'-demethyl-4'-O-(3,4,5-trimethoxyphenylcinnamoyl)-1-deoxypodophyllotoxin;
4'-demethyl-4'-O-(4-dimethylaminophenylacetyl)-1-deoxypodophyllotoxin;
4'-demethyl-4'-O-acetyl-1-deoxypodophyllotoxin;
4'-demethyl-4'-O-propanoyl-1-deoxypodophyllotoxin;
4'-demethyl-4'-O-butanoyl-1-deoxypodophyllotoxin;
4'-demethyl-4'-O-(3'-methylbutanoyl)-1-deoxypodophyllotoxin;
4'-demethyl-4'-O-heptanoyl-1-deoxypodophyllotoxin;
4'-demethyl-4'-O-octanoyl-1-deoxypodophyllotoxin;
4'-demethyl-4'-O-decanoyl-1-deoxypodophyllotoxin;
4'-demethyl-4'-O-benzoyl-1-deoxypodophyllotoxin;
4'-demethyl-4'-O-dodecanoyl-1-deoxypodophyllotoxin;
4'-demethyl-4'-O-tetradecanoyl-1-deoxypodophyllotoxin;
4'-demethyl-4'-O-hexadecanoyl-1-deoxypodophyllotoxin;
4'-demethyl-4'-O-(cis-9'-hexadecenoyl)-1-deoxypodophyllotoxin;
4'-demethyl-4'-O-octadecanoyl-1-deoxypodophyllotoxin;
4'-demethyl-4'-O-(cis-9'-octadecenoyl)-1-deoxypodophyllotoxin;
4'-demethyl-4'-O-(trans-9'-octadecenoyl)-1-deoxypodophyllotoxin;
4'-demethyl-4'-O-(cis-11'-octadecenoyl)-1-deoxypodophyllotoxin;
4'-demethyl-4'-O-(trans-11'-octadecenoyl)-1-deoxypodophyllotoxin;
4'-demethyl-4'-O-(cis,cis-9',12'-octadecadienoyl)-1-deoxypodophyllotoxin;
4'-demethyl-4'-O-(trans,trans-9',12'-octadecadienoyl)-1-deoxypodophyllotoxin;
4'-demethyl-4'-O-(cis-9',12',15'-octadecatrienoyl)-1-deoxypodophyllotoxin;
4'-demethyl-4'-O-(cis-6',9',12'-octadecatrienoyl)-1-deoxypodophyllotoxin;
4'-demethyl-4'-O-eicosanoyl-1-deoxypodophyllotoxin;
4'-demethyl-4'-O-(cis-11'-eicosenoyl)-1-deoxypodophyllotoxin;
4'-demethyl-4'-O-(trans-11'-eicosenoyl)-1-deoxypodophyllotoxin;
4'-demethyl-4'-O-(cis,cis-11',14'-eicosadienoyl)-1-deoxypodophyllotoxin;
4'-demethyl-4'-O-(cis-5',8',11',14'-eicosatetraenoyl)-1-deoxypodophyllotoxin;
4'-demethyl-4'-O-docosanoyl-1-deoxypodophyllotoxin;
4'-demethyl-4'-O-(cis-13'-docosenoyl)-1-deoxypodophyllotoxin;

4'-demethyl-4'-O-(cis-4',7',10',13',16',19'-docosahexaenoyl)-1-deoxypodophyllotoxin;

4'-demethyl-4'-O-retinoyl-1-deoxypodophyllotoxin;

4'-demethyl-4'-O-(5'-carboxy-pentanoyl)-1-deoxypodophyllotoxin;

4'-demethyl-4'-O-(7'-carboxy-heptanoyl)-1-deoxypodophyllotoxin;

4'-demethyl-4'-O-(9'-carboxy-nonanoyl)-1-deoxypodophyllotoxin;

4'-demethyl-4'-O-(11'-carboxy-undecanoyl)-1-deoxypodophyllotoxin;

4'-demethyl-4'-O-(13'-carboxy-tridecanoyl)-1-deoxypodophyllotoxin; and

4'-demethyl-4'-O-(15'-carboxy-pentadecanoyl)-1-deoxypodophyllotoxin.

The compounds of the present invention may be divided into three groups depending on the substituent R as follows:

(1) Compounds wherein R is -A-$NH_2$ [Compound of the following formula (1a), wherein A is defined as previously described];

(1a)

(2) Compounds wherein R is —NH—$R^1$ [Compound of the following formula (1b), wherein $R^1$ is defined as previously described]; and (1b)

(3) Compounds wherein R is phenyl-$C_{2-4}$alkenyl unsubstituted or substituted by 1 to 5 $C_{1-4}$alkoxy; benzyl unsubstituted or substituted by amino or di$C_{1-4}$alkylamino; straight-chain or branched $C_{1-21}$alkyl, $C_{15-21}$alkenyl, $C_{15-21}$alkadienyl, $C_{15-21}$alkatrienyl, $C_{15-21}$alkatetraenyl, or $C_{15-21}$alkahexaenyl; retinyl; or $C_{5-15}$carboxyalkyl [Compound of the following formula (1c)].

(1c)

in which

A represents amino acid residue, —$(CH_2)_{n1}$—; or —$(CH_2)_{n2}$—$C_6H_5$, wherein n1 denotes an integer of 2 to 8, n2 denotes an integer of 1 to 4, $R^1$ represents straight-chain or branched $C_{1-4}$alkyl unsubstituted or substituted by substituent(s) selected from a group consisting of halogen and hydroxy; cycloalkyl; haloacetyl; allyl; phenyl unsubstituted or substituted by substituent(s) selected from a group consisting of halogen, $C_{1-4}$alkoxy, $C_{1-4}$alkyl and $C_{1-4}$alkylthio; benzyl; benzoyl; or benzenesulfonyl, and $R^2$ represents phenyl-$C_{2-4}$alkenyl unsubstituted or substituted by 1 to 5 $C_{1-4}$alkoxy; benzyl unsubstituted or substituted by amino or di$C_{1-4}$alkylamino; straight-chain or branched $C_{1-21}$alkyl, $C_{15-21}$alkenyl, $C_{15-21}$alkadienyl, $C_{15-21}$alkatrienyl, $C_{15-21}$alkatetraenyl, or $C_{15-21}$alkahexaenyl; retinyl; or $C_{5-15}$carboxyalkyl.

The process for preparing each of the compounds is as follows.

(1) Preparation of the Compound of Formula (1a)

First, according to a known procedure [see, Laurent, D. et al.; J. Med. Chem., 41, 4475–4485, 1998], 4'-demethyl-1-deoxypodophyllotoxin (DDPT) of the following formula (3):

(3)

is prepared from deoxypodophyllotoxin (DPT) of the following formula (2) (see Preparation 1):

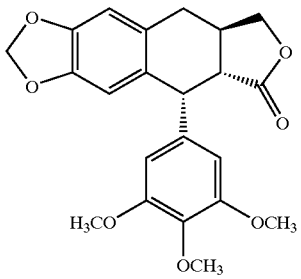
(2)

Then, DDPT of formula (3) is esterified in an inert solvent and optionally in the presence of a condensing agent and an organic base with a compound of the following formula (4):

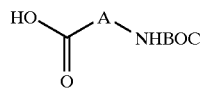
(4)

in which
A is defined as previously described, and
BOC means t-butoxycarbonyl, to give a compound of the following formula (5):

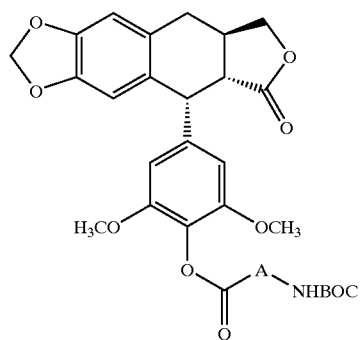
(5)

in which
A and BOC are defined as previously described.

In preparing the compound of formula (1a), 4'-OH group of DDPT of formula (3) cannot be directly esterified with a compound of the following formula (6):

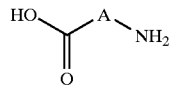
(6)

Therefore, the compound of formula (4) is prepared in advance by introducing an amino-protecting group, for example, t-butoxycarbonyl (BOC) into the amino group of the compound of formula (6) (see Preparations 2~17 and Reaction Scheme 1).

The organic base which can be used in the above reaction includes trialkylamines such as trimethylamine, triethylamine, N,N-diisopropyl-N-ethylamine, etc. and pyridines such as pyridine, picoline, 4-dimethylaminopyridine, etc. 4-Dimethylaminopyridine among them is the most preferable. Conventional condensing agents may be used, and dicyclohexylcarbodiimide (DCC) is most preferable.

The above reaction is generally carried out in a solvent which does not adversely affect the reaction. As the solvent which can be preferably used for this purpose, haloalkane solvents, benzene solvents, nitrile solvents, or ether solvents, for example, dichloromethane, dichloroethane, acetone, dioxane, acetonitrile, tetrahydrofuran, etc. can be mentioned. Particularly preferable solvents among them are haloalkane solvents such as dichloromethane. When the solvents are used in an anhydrous state in the above reaction, the reaction yield may be raised. Therefore, anhydrous dichloromethane is most preferable.

The yield is much higher when the above reaction is carried out under cooling rather than under room temperature or warming.

The condensing agent and organic base used in the above reaction are respectively used in the amount of about 1 to 10 molar equivalents, preferably 5 molar equivalents with respect to the starting material.

The reaction time for esterification is typically 2 to 3 hours. However, in the present reaction, since the yield abruptly decreases due to the formation of side products as the reaction time exceeds 30 minutes, it is preferable to react for about 30 minutes.

The compound of formula (5) prepared by the above reaction is novel.

Then, the compound of formula (5) is deprotected in a solvent to give the desired compound of formula (1a) (see Examples 1 to 14).

Protecting groups, for example, t-BOC group may be removed by using acids, such as for example, hydrochloric acid, sulfuric acid, or trifluoroacetic acid, trialkylsilyl halides, such as for example, trimethylsilyl iodide or trimethylsilyl chloride, or metal halides, such as for example, aluminum chloride, etc.

As the solvent, any inert organic solvent which does not adversely affect the reaction, preferably dichloromethane containing trifluoroacetic acid is used.

(2) Preparation of the Compound of Formula (1b)

DDPT of formula (3) is reacted in an inert solvent and optionally in the presence of an organic base with an isocyanate of the following formula (7):

(7)

in which $R^1$ represents straight-chain or branched $C_{1-4}$alkyl unsubstituted or substituted by substituent(s) selected from a group consisting of halogen and hydroxy; cycloalkyl; haloacetyl; allyl; phenyl unsubstituted or substituted by substituent(s) selected from a group consisting of halogen, $C_{1-4}$alkoxy, $C_{1-4}$alkyl and $C_{1-4}$alkylthio; benzyl; benzoyl; or benzenesulfonyl, to give the compound of the following formula (1b) (see Examples 15 to 30):

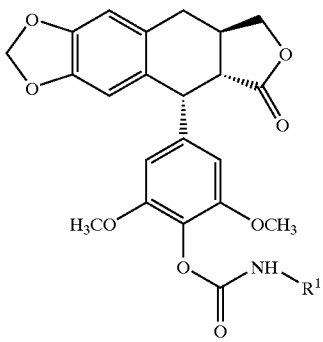

(1b)

in which R¹ is defined as previously described.

The organic base which can be used in the above reaction includes trialkylamines such as trimethylamine, triethylamine, N,N-diisopropyl-N-ethylamine, etc. and pyridines such as pyridine, picoline, 4-dimethylaminopyridine, etc. Triethylamine (TEA) among them is the most preferable.

The above reaction is generally carried out in a solvent which does not adversely affect the reaction. As the solvent which can be preferably used for this purpose, haloalkane solvents, benzene solvents, nitrile solvents, or ether solvents, for example, dichloromethane, dichloroethane, acetone, dioxane, acetonitrile, tetrahydrofuran, etc. can be mentioned. Particularly preferable solvents among them are haloalkane solvents such as dichloromethane. When the solvents are used in an anhydrous state in the above reaction, the reaction yield may be raised. Therefore, anhydrous dichloromethane is most preferable.

The yield is much higher when the above reaction is carried out under cooling rather than under room temperature or warming.

(3) Preparation of the Compound of Formula (1c)

DDPT of formula (3) is esterified in an inert solvent and optionally in the presence of a condensing agent and an organic base with a compound of the following formula (8):

R²—COOH            (8)

in which R² represents phenyl-C$_{2-4}$alkenyl unsubstituted or substituted by 1 to 5 C$_{1-4}$alkoxy; benzyl unsubstituted or substituted by amino or diC$_{1-4}$alkylamino; straight-chain or branched C$_{1-21}$alkyl, C$_{15-21}$alkenyl, C$_{15-21}$alkadienyl, C$_{15-21}$alkatrienyl, C$_{15-21}$alkatetraenyl, or C$_{15-21}$alkahexaenyl; retinyl; or C$_{5-15}$carboxyalkyl, to give the compound of the following formula (1c) (see Examples 31 to 68):

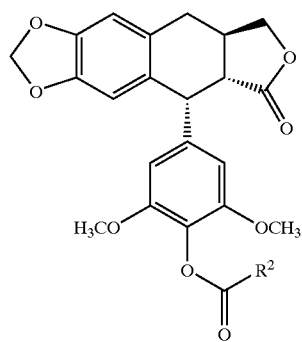

(1c)

in which R² is defined as previously described.

The reaction conditions of the above reaction are the same as those of the reaction for preparing the compound of formula (1a).

The final products obtained in the above process variants (1), (2) and (3) can be further purified by conventional purification methods, such as for example, recrystallization, distillation, chromatography, etc.

The above processes are depicted in the following Reaction Schemes 1 to 4.

Reaction Scheme 1:
Process for preparing the compound of formula (4)

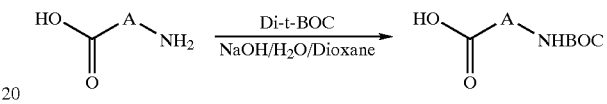

Reaction Scheme 2:
Process for preparing the compound of (1a)

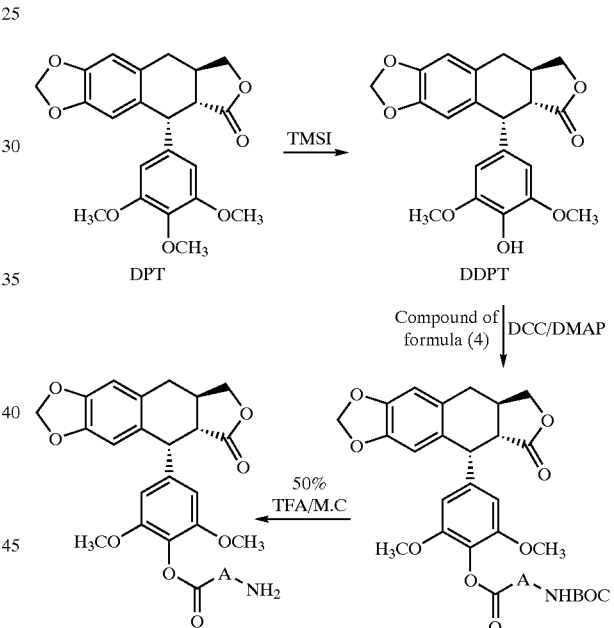

Reaction Scheme 3:
Process for preparing the compound of formula (1b)

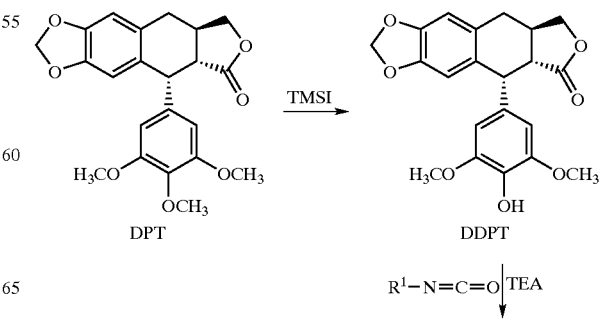

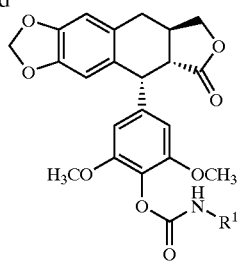

Reaction Scheme 4:
Process of preparing the compound of formula (1c)

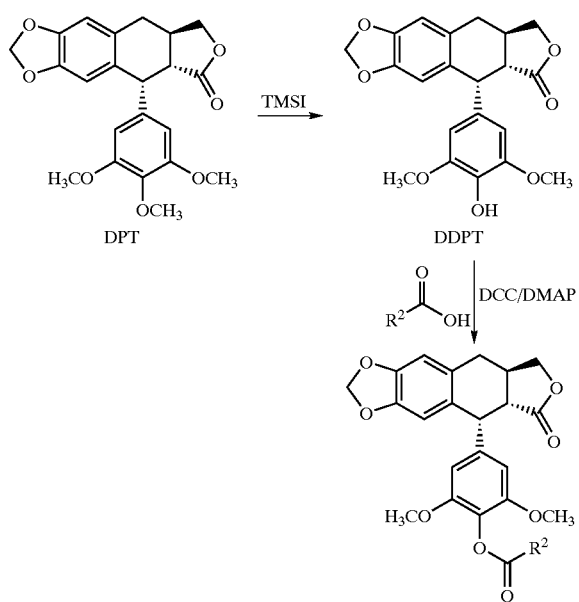

in which
A, $R^1$, $R^2$ and BOC are defined as previously described,
TMSI means trimethylsilyl,
DCC means dicyclohexylcarbodiimide,
DMAP means 4-dimethylaminopyridine,
TFA means trifluoroacetic acid,
M.C means methylene chloride, and
TEA means triethylamine.

The compound of formula (1) of the present invention has a potent anticancer activity as verified in the following experimental examples. Therefore, the present invention provides an anticancer composition comprising the compound of formula (1).

When the compound of the present invention is used for clinical purpose, it is preferably administered in the amount ranging from 0.5 to 5 µg, preferably 1.5 to 3.5 mg, per kg of body weight a day. However, the specific administration dosage for the patient can be varied with the specific compound used, body weight, sex, hygienic condition or diet of the subject patient, time or method of administration, mixing ratio of the agent, severity of the disease to be treated, etc.

The compound of the present invention may be administered in the form of injections or oral preparations. These preparations may be prepared according to the conventional methods. Injections, for example, sterilized aqueous or oily suspension for injection, can be prepared according to the known procedure using suitable dispersing agent, wetting agent, or suspending agent. Solvents which can be used for preparing injections include conventional solvents or suspending media such as water, sterilized fixing oil, etc.

The present invention will be more specifically explained in the following preparations, examples and experiments. However, it should be understood that the scope of the present invention is not limited to them in any manner.

Preparation 1

Synthesis of 4'-demethyl-1-deoxypodophyllotoxin (DDPT)

4-Methoxy group of deoxypodophyllotoxin (DPT) was selectively demethylated according to a known process [see, Laurent, D. et al.; J. Med. Chem., 41, 4475–4485, 1998] to give deoxypodophyllotoxin (DPT). The reaction procedures are described in detail in the following.

Deoxypodophyllotoxin (3.98 g, 10 mmol) was dissolved in anhydrous dichloromethane (100 ml) and the temperature was adjusted to 0° C. Then, a solution of trimethylsilyl iodide (4.25 ml, 30 mmol) in anhydrous dichloromethane (10 ml) was added dropwise thereto for 30 minutes under stirring. The reactants and barium carbonate (2 g) were added to a solvent mixture (300 ml) of acetone and water (acetone:water=150 ml:150 ml) and stirred for 30 minutes. The reaction mixture was extracted with dichloromethane (200 ml). The extract was dried over anhydrous sodium sulfate and concentrated under reduced pressure. The crude product thus obtained was purified by silica gel column (3×'20 cm) (eluent: cyclohexane:ethyl acetate=2:1, v/v) to give 2.76 g of the title compound.

Yield: 72%.

$^1$H-NMR (ppm): d 8.24 (s, 1H), 6.74 (s, 1H), 6.49 (s, 1H), 6.24 (s, 2H), 5.96 (d, J=1.3 Hz, 1H), 5.94 (d, J=1.3 Hz, 1H), 4.45 (d, J=4.6 Hz, 1H), 4.20–4.44 (m, 1H), 3.72–4.04 (m, 1H), 3.64 (s, 6H), 2.52–3.20 (m, 4H).

IR (KBr, cm$^{-1}$); 3396, 1764.

Preparation 2

Synthesis of N-t-butyloxycarbonyl-alanine (4-1)

L-alanine (445 mg, 5 mmol) was dissolved in a solvent mixture of 1N NaOH (17 ml), distilled water (9 ml) and 1,4-dioxane (17 ml) and cooled to 0° C. Di-t-butyl dicarbonate (1.2 g, 5.5 mmol) was added for about 5 minutes bit by bit. The reaction solution was stirred for about 5 minutes at 0° C., warmed to room temperature, and then stirred for further about 2 hours. The reaction solution was concentrated under reduced pressure to remove 1,4-dioxane. To the remaining solution was added 1N-HCl to make the solution acidic. The remaining solution was extracted three times with ethyl acetate (30 ml×3). The extracts were combined, dried over anhydrous sodium sulfate, and concentrated under reduced pressure to give 850 mg of the title compound, which was not purified any more.

Yield: 90%.

$^1$H-NMR (ppm): 10.5 (br, 1H), 5.3 (br, 1H), 4.64 (d, J=7.5 Hz, 3H), 1.48 (n, 1H), 1.46 (s, 9H).

IR (KBr, cm$^{-1}$); 3390, 1755, 1710.

Preparation 3

Synthesis of N-t-butyloxycarbonyl-leucine (4-2)

The same procedure as Preparation 2 was carried out except that DL-leucine (655 mg, 5 mmol) was used to give 1.06 g of the title compound.

Yield: 93%.

Preparation 4

Synthesis of N-t-butyloxycarbonyl-valine (4-3)

The same procedure as Preparation 2 was carried out except that L-valine (585 mg, 5 mmol) was used to give 966 mg of the title compound.

Yield: 89%.

Preparation 5

Synthesis of N-t-butyloxycarbonyl-glycine (4-4)

The same procedure as Preparation 2 was carried out except that glycine (375 mg, 5 mmol) was used to give 805 mg of the title compound.

Yield: 92%.

Preparation 6

Synthesis of N-t-butyloxycarbonyl-serine (4-5)

The same procedure as Preparation 2 was carried out except that L-serine (525 mg, 5 mmol) was used to give 810 mg of the title compound.

Yield: 79%.

Preparation 7

Synthesis of N-t-butyloxycarbonyl-methionine (4-6)

The same procedure as Preparation 2 was carried out except that L-methionine (745 mg, 5 mmol) was used to give 1.17 g of the title compound.

Yield: 94%.

Preparation 8

Synthesis of N-t-butyloxycarbonyl-phenylalanine (4-7)

The same procedure as Preparation 2 was carried out except that L-phenylalanine (825 mg, 5 mmol) was used to give 1.19 g of the title compound.

Yield: 90%.

Preparation 9

Synthesis of N-t-butyloxycarbonyl-threonine (4-8)

The same procedure as Preparation 2 was carried out except that L-threonine (595 mg, 5 mmol) was used to give 900 mg of the title compound.

Yield: 82%.

Preparation 10

Synthesis of N-t-butyloxycarbonyl-tyrosine (4-9)

The same procedure as Preparation 2 was carried out except that DL-tyrosine (905 mg, 5 mmol) was used to give 913 mg of the title compound.

Yield: 65%.

Preparation 11

Synthesis of 3-t-butyloxycarbonylamino-propanoic acid (4-10)

The same procedure as Preparation 2 was carried out except that 3-aminopropanoic acid (445 mg, 5 mmol) was used to give 900 mg of the title compound.

Yield: 95%.

$^1$H-NMR (ppm): 10.1 (br, 1H), 5.1 (br, 1H), 3.29 (dd, J=5.8, 12.7 Hz, 2H), 2.56 (t, J=111.7 Hz, 2H), 1.45 (s, 9H).

IR (KBr, cm$^{-1}$); 3390, 1750, 1720.

Preparation 12

Synthesis of 4-t-butyloxycarbonylamino-butanoic acid (4-11)

The same procedure as Preparation 2 was carried out except that 4-aminobutanoic acid (515 mg, 5 mmol) was used to give 954 mg of the title compound.

Yield: 94%.

Preparation 13

Synthesis of 5-t-butyloxycarbonylamino-pentanoic acid (4-12)

The same procedure as Preparation 2 was carried out except that 5-aminopentanoic acid (585 mg, 5 mmol) was used to give 998 mg of the title compound.

Yield: 92%.

Preparation 14

Synthesis of 6-t-butyloxycarbonylamino-hexanoic acid (4-13)

The same procedure as Preparation 2 was carried out except that 6-aminohexanoic acid (655 mg, 5 mmol) was used to give 1.04 g of the title compound.

Yield: 90%.

Preparation 15

Synthesis of 7-t-butyloxycarbonylamino-heptanoic acid (4-14)

The same procedure as Preparation 2 was carried out except that 7-aminoheptanoic acid (725 mg, 5 mmol) was used to give 1.09 g of the title compound.

Yield: 89%.

Preparation 16

Synthesis of 8-t-butyloxycarbonylamino-octanoic acid (4-15)

The same procedure as Preparation 2 was carried out except that 8-aminooctanoic acid (795 mg, 5 mmol) was used to give 1.14 g of the title compound.

Yield: 93%.

Preparation 17

Synthesis of 4-t-butyloxycarbonylamino-phenylacetic acid (4-16)

The same procedure as Preparation 2 was carried out except that 4-aminophenylacetic acid (835 mg, 5 mmol) was used to give 1.26 g of the title compound.

Yield: 94%.

EXAMPLE 1

Synthesis of 4'-demethyl-4'-O-alanoyl-1-deoxypodophyllotoxin (1a-1)

To a 50 ml round-bottomed flask were introduced 4'-demethyl-1-deoxypodophyllotoxin (DDPT, 384 mg, 1 mmol), dicyclohexylcarbodiimide (DCC, 1.03 g, 5 mmol), and 4-dimethylaminopyridine (4-DMAP, 306 mg, 2.5 mmol), which was then dissolved in anhydrous dichloromethane (20 ml). Under 4° C. and nitrogen gas, N-t-butoxycarbonyl-alanine (189 mg, 1 mmol) was added thereto and the resulting mixture was stirred for 1 hour. To the reaction mixture was added distilled water (100 ml). The resulting mixture was extracted three times with dichloromethane (100 ml). The extracts were combined, dried over anhydrous sodium sulfate, and concentrated under reduced pressure. The resulting crude product, without any process of purification, was directly dissolved in anhydrous dichloromethane containing 50% trifluoroacetic acid (20 ml) and stirred at room temperature for 2 hours. The reaction solution was concentrated under reduced pressure to give a crude product, which was then purified by silica gel column (1×'15 cm) (eluent: dichloromethane:methanol=9.5:0.5, v/v) to give 370 mg of the title compound.

Yield: 81.3%.

$^1$H-NMR (ppm): d 7.67 (br, 2H, —NH$_2$), 6.65 (s, 1H), 6.42 (s, 1H), 6.36 (s, 2H), 5.94 (d, J=1.3 Hz, 1H), 5.92 (d, J=1.3 Hz, 1H), 4.54 (d, J=3.81 Hz, 1H), 4.36 (t, J=16.3 Hz, 1H), 3.85 (t, J=16.3 Hz, 1H), 3.69~3.58 (m, 7H), 3.02~2.70 (m, 4H), 1.59 (d, J=5.79 Hz, 3H).

EXAMPLE 2

Synthesis of 4'-demethyl-4'-O-leucinoyl-1-deoxypodophyllotoxin (1a-2)

The same procedure as Example 1 was carried out except that N-t-butyloxycarbonylleucine (231 mg, 1 mmol) was used to give 403 mg of the title compound.

Yield: 81.2%.

$^1$H-NMR (ppm): d 7.76 (br, 2H, —NH$_2$), 6.65 (s, 1H), 6.41 (s, 1H), 6.36 (s, 2H), 5.93 (d, J=1.3 Hz, 1H), 5.91 (d, J=1.3 Hz, 1H), 4.55 (d, J=3.88 Hz, 1H), 4.36 (t, J=16.1 Hz, 1H), 3.84 (t, J=16.1 Hz, 1H), 3.70~3.50 (m, 7H), 3.03~2.71 (m, 4H), 1.90~1.71 (m, 3H), 1.06 (d, J=5.89 Hz, 6H).

EXAMPLE 3

Synthesis of 4'-demethyl-4'-O-valinoyl-1-deoxypodophyllotoxin (1a-3)

The same procedure as Example 1 was carried out except that N-t-butyloxycarbonylvaline (217 mg, 1 mmol) was used to give 406 mg of the title compound.

Yield: 84%.

$^1$H-NMR (ppm): d 7.76 (br, 2H, —NH$_2$), 6.64 (s, 1H), 6.41 (s, 1H), 6.37 (s, 2H), 5.93 (d, J=1.3 Hz, 1H), 5.91 (d, J=1.3 Hz, 1H), 4.52 (d, J=3.81 Hz, 1H), 4.37 (t, J=16.3 Hz, 1H), 3.86 (t, J=16.3 Hz, 1H), 3.72 (s, 6H), 3.48 (m, 1H), 3.03~2.71 (m, 4H), 2.39 (m, 1H), 1.06 (d, J=6.99 Hz, 6H).

EXAMPLE 4

Synthesis of 4'-demethyl-4'-O-glycinoyl-1-deoxypodophyllotoxin (1a-4)

The same procedure as Example 1 was carried out except that N-t-butyloxycarbonylglycine (175 mg, 1 mmol) was used to give 366 mg of the title compound.

Yield: 83%.

$^1$H-NMR (ppm): d 7.68 (br, 2H, —NH$_2$), 6.66 (s, 1H), 6.41 (s, 1H), 6.38 (s, 2H), 5.94 (d, J=1.3 Hz, 1H), 5.92 (d, J=1.3 Hz, 1H), 4.52 (d, J=3.88 Hz, 1H), 4.38 (t, J=16.1 Hz, 1H), 3.87 (t, J=16.1 Hz, 1H), 3.68~3.57 (m, 8H), 3.07~2.75 (m, 4H).

EXAMPLE 5

Synthesis of 4'-demethyl-4'-O-serinoyl-1-deoxypodophyllotoxin (1a-5)

The same procedure as Example 1 was carried out except that N-t-butyloxycarbonylserine (205 mg, 1 mmol) was used to give 334 mg of the title compound.

Yield: 71%.

$^1$H-NMR (ppm): d 7.67 (br, 2H, —NH$_2$), 6.68 (s, 1H), 6.43 (s, 1H), 6.38 (s, 2H), 5.94 (d, J=1.3 Hz, 1H), 5.92 (d, J=1.3 Hz, 1H), 4.49 (d, J=3.81 Hz, 1H), 4.34 (t, J=16.9 Hz, 1H), 4.02~3.58 (m, 10H), 3.08~2.76 (m, 4H).

EXAMPLE 6

Synthesis of 4'-demethyl-4'-O-phenylalanoyl-1-deoxypodophyllotoxin (1a-7)

The same procedure as Example 1 was carried out except that N-t-butyloxycarbonylphenylalanine (265 mg, 1 mmol) was used to give 420 mg of the title compound.

Yield: 79%.

$^1$H-NMR (ppm): d 7.37~7.18 (m, 5H), 6.66 (s, 1H), 6.46 (s, 1H), 6.38 (s, 2H), 6.23 (br, 2H, —NH$_2$), 5.91 (s, 2H), 4.57 (s, 1H), 4.47 (m, 2H), 3.95 (m, 1H), 3.66 (s, 6H), 3.37 (d, J=5.66 Hz, 2H), 3.02~2.71 (m, 4H).

EXAMPLE 7

Synthesis of 4'-demethyl-4'-O-tyrosinoyl-1-deoxypodophyllotoxin (1a-9)

The same procedure as Example 1 was carried out except that N-t-butyloxycarbonyltyrosine (281 mg, 1 mmol) was used to give 383 mg of the title compound.

Yield: 70%.

$^1$H-NMR (ppm): d 6.95 (d, J=8.88 Hz, 2H), 6.68 (d, J=8.88 Hz, 2H), 6.65 (s, 1H), 6.44 (s, 1H), 6.39 (s, 2H), 6.24 (br, 2H, —NH$_2$), 5.92 (s, 2H), 4.54 (s, 1H), 4.46 (m, 1H), 3.95~3.84 (m, 2H), 3.66 (s, 6H), 3.04~2.70 (m, 6H).

EXAMPLE 8

Synthesis of 4'-demethyl-4'-O-(3-aminopropanoyl)-1-deoxypodophyllotoxin (1a-10)

The same procedure as Example 1 was carried out except that 3-(t-butyloxycarbonylamino)propionic acid (189 mg, 1 mmol) was used to give 382 mg of the title compound.

Yield: 84%.

$^1$H-NMR (ppm): d 7.67 (br, 2H, —NH$_2$), 6.67 (s, 1H), 6.46 (s, 1H), 6.37 (s, 2H), 5.92 (s, 2H), 4.56 (s, 1H), 4.39 (m, 1H), 3.96 (m, 1H), 3.68 (m, 6H), 3.04~2.88 (m, 6H), 2.49 (t, J=11.7 Hz, 2H).

EXAMPLE 9

Synthesis of 4'-demethyl-4'-O-(4-aminobutanoyl)-1-deoxypodophyllotoxin (1a-1)

The same procedure as Example 1 was carried out except that 4-(t-butyloxycarbonylamino)butanoic acid (203 mg, 1 mmol) was used to give 385 mg of the title compound.

Yield: 82%.

$^1$H-NMR (ppm): d 7.75 (br, 2H, —NH$_2$), 6.64 (s, 1H), 6.44 (s, 1H), 6.36 (s, 2H), 5.90 (s, 2H), 4.54 (s, 1H), 4.32 (m, 1H), 3.91~3.64 (m, 7H), 3.10~2.61 (m, 8H), 2.04 (m, 2H).

EXAMPLE 10

Synthesis of 4'-demethyl-4'-O-(5-aminopentanoyl)-1-deoxypodophyllotoxin (1a-12)

The same procedure as Example 1 was carried out except that 5-(t-butyloxycarbonylamino)pentanoic acid (217 mg, 1 mmol) was used to give 386 mg of the title compound.

Yield: 80%.

$^1$H-NMR (ppm): d 7.77 (br, 2H, —NH$_2$), 6.65 (s, 1H), 6.45 (s, 1H), 6.39 (s, 2H), 5.92 (s, 2H), 4.51 (s, 1H), 4.38 (m, 1H), 3.90~3.68 (m, 7H), 3.09~2.58 (m, 8H), 1.88 (m, 4H).

EXAMPLE 11

Synthesis of 4'-demethyl-4'-O-(6-aminohexanoyl)-1-deoxypodophyllotoxin (1a-13)

The same procedure as Example 1 was carried out except that 6-(t-butyloxycarbonylamino)hexanoic acid (231 mg, 1 mmol) was used to give 408 mg of the title compound.

Yield: 82%.

$^1$H-NMR (ppm): d 7.68 (br, 2H, —NH$_2$), 6.65 (s, 1H), 6.49 (s, 1H), 6.37 (s, 2H), 5.92 (s, 2H), 4.58 (s, 1H), 4.39 (m, 1H), 3.90~3.66 (m, 7H), 3.02~2.54 (m, 8H), 1.54 (m, 6H).

EXAMPLE 12

Synthesis of 4'-demethyl-4'-O-(7-aminoheptanoyl)-1-deoxypodophyllotoxin (1a-14)

The same procedure as Example 1 was carried out except that 7-(t-butyloxycarbonylamino)heptanoic acid (245 mg, 1 mmol) was used to give 404 mg of the title compound.

Yield: 79%.

$^1$H-NMR (ppm): d 7.78 (br, 2H, —NH$_2$), 6.65 (s, 1H), 6.44 (s, 1H), 6.37 (s, 2H), 5.93 (s, 2H), 4.57 (s, 1H), 4.40 (m, 1H), 3.89~3.67 (m, 7H), 2.99~2.54 (m, 8H), 1.58 (m, 8H).

EXAMPLE 13

Synthesis of 4'-demethyl-4'-O-(8-aminooctanoyl)-1-deoxypodophyllotoxin (1a-15)

The same procedure as Example 1 was carried out except that 8-(t-butyloxycarbonylamino)octanoic acid (259 mg, 1 mmol) was used to give 405 mg of the title compound.

Yield: 78%.

$^1$H-NMR (ppm): d 7.69 (br, 2H, —NH$_2$), 6.64 (s, 1H), 6.49 (s, 1H), 6.36 (s, 2H), 5.91 (s, 2H), 4.52 (s, 1H), 4.35 (m, 1H), 3.89~3.67 (m, 7H), 3.11~2.58 (m, 8H), 1.57 (m, 10H).

EXAMPLE 14

Synthesis of 4'-demethyl-4'-O-(4-aminophenylacetyl)-1-deoxypodophyllotoxin (1a-16)

The same procedure as Example 1 was carried out except that 4-(t-butyloxycarbonylamino)phenylacetic acid (251 mg, 1 mmol) was used to give 320 mg of the title compound.

Yield: 64%.

$^1$H-NMR (ppm): d 7.25 (d, J=8.96 Hz, 2H), 7.05 (d, J=8.96 Hz, 2H), 6.65 (s, 1H), 6.50 (s, 1H), 6.37 (s, 2H), 5.92 (s, 2H), 4.59 (s, 1H), 4.43 (m, 1H), 3.91~3.82 (m, 3H), 3.68 (s, 3H), 3.66 (s, 3H), 3.01~2.73 (m, 4H).

EXAMPLE 15

Synthesis of 4'-demethyl-4'-O-ethylcarbamoyl-1-deoxypodophyllotoxin (1b-1)

To a 50 ml round-bottomed flask were introduced 4'-demethyldeoxy-podophyllotoxin (384 mg, 1 mmol), ethyl isocyanate (355 mg, 5 mmol), and triethylamine (700 ml, 5 mmol), which was then dissolved in anhydrous dichloromethane (20 ml). The reaction mixture was stirred for 1 hour under 4° C. and nitrogen gas. To the reaction mixture was added distilled water (100 ml). The resulting mixture was extracted three times with dichloromethane (80 ml). The extracts were combined, dried over anhydrous sodium sulfate, and concentrated under reduced pressure. The resulting crude product was purified by silica gel column (1×'5 cm) (eluent:cyclohexane:ethyl acetate=3:1, v/v) to give 405 mg of the title compound.

Yield: 89%.

$^1$H-NMR (ppm): d 6.66 (s, 1H), 6.51 (s, 1H), 6.38 (s, 2H), 5.93 (s, 2H), 4.96 (br, 1H, —NH), 4.63 (s, 1H), 4.45 (m, 1H), 3.99~3.72 (m, 8H), 3.14~2.72 (m, 4H), 1.21 (d, J=6.35 Hz, 6H).

EXAMPLE 16

Synthesis of 4'-demethyl-4'-O-isopropylcarbamoyl-1-deoxypodophyllotoxin (1b-2)

The same procedure as Example 15 was carried out except that isopropylisocyanate (425 mg, 5 mmol) was used to give 370 mg of the title compound.

Yield: 79%.

$^1$H-NMR (ppm): d 6.66 (s, 1H), 6.51 (s, 1H), 6.38 (s, 2H), 5.93 (s, 2H), 4.96 (br, 1H, —NH), 4.63 (s, 1H), 4.45 (m, 1H), 3.99~3.72 (m, 8H), 3.14~2.72 (m, 4H), 1.21 (d, J=6.35 Hz, 6H).

EXAMPLE 17

Synthesis of 4'-demethyl-4'-O-(2-chloroethylcarbamoyl)-1-deoxypodophyllotoxin (1b-3)

The same procedure as Example 15 was carried out except that 2-chloroethylisocyanate (525 mg, 5 mmol) was used to give 380 mg of the title compound.

Yield: 78%.

$^1$H-NMR (ppm): d 6.67 (s, 1H), 6.53 (s, 1H), 6.37 (s, 2H), 5.91 (s, 2H), 4.92 (br, 1H, —NH), 4.66 (s, 1H), 4.43 (m, 1H), 3.98~3.62 (m, 9H), 3.24~2.72 (m, 6H).

EXAMPLE 18

Synthesis of 4'-demethyl-4'-O-cyclohexylcarbamoyl-1-deoxypodophyllotoxin (1b-4)

The same procedure as Example 15 was carried out except that cyclohexylisocyanate (125 mg, 1 mmol) was used to give 460 mg of the title compound.

Yield: 90%.

$^1$H-NMR (ppm): d 6.66 (s, 1H), 6.53 (s, 1H), 6.37 (s, 2H), 5.91 (s, 2H), 5.05 (br, 1H, —NH), 4.63 (s, 1H), 4.45 (m, 1H), 3.98~3.57 (m, 8H), 3.09~2.71 (m, 2H), 1.96~1.17 (m, 10H).

EXAMPLE 19

Synthesis of 4'-demethyl-4'-O-(2-hydroxyethyl)carbamoyl-1-deoxypodophyllotoxin (1b-5)

To a 50 ml round-bottomed flask were introduced 4'-demethyldeoxy-podophyllotoxin (384 mg, 1 mmol), phenoxyacetylchloride (625 ml, 5 mmol), and triethylamine (700 ml, 5 mmol), which was then dissolved in anhydrous dichloromethane (20 ml). The reaction mixture was stirred for 1 hour under 4° C. and nitrogen gas. To the reaction mixture was added distilled water (100 ml). The resulting mixture was extracted three times with dichloromethane (80 ml). The extracts were combined, dried over anhydrous sodium sulfate, and concentrated under reduced pressure. The resulting crude product was dissolved in absolute ethanol (30 ml), ethanolamine (91.5 mg, 1.5 mmol) was added thereto, and the mixture was stirred at room temperature for 3 hours. The reaction solution was concentrated under reduced pressure and the residue was purified by silica gel column (1×'5 cm) (eluent: cyclohexane:ethyl acetate=1:1, v/v) to give 245 mg of the title compound.

Yield: 52%.

$^1$H-NMR (ppm): d 6.68 (s, 1H), 6.53 (s, 1H), 6.39 (s, 2H), 5.93 (s, 2H), 4.90 (br, 1H, —NH), 4.60 (s, 1H), 4.41 (m, 1H), 3.99~3.62 (m, 9H), 3.25~2.69 (m, 6H).

EXAMPLE 20

Synthesis of 4'-demethyl-4'-O-chloroacetylcarbamoyl-1-deoxypodophyllotoxin (1b-6)

The same procedure as Example 15 was carried out except that chloroacetylisocyanate (119 mg, 1 mmol) was used to give 300 mg of the title compound.

Yield: 60%.

$^1$H-NMR (ppm): d 6.66 (s, 1H), 6.52 (s, 1H), 6.39 (s, 2H), 5.92 (s, 2H), 5.12 (br, 1H, —NH), 4.60 (s, 1H), 4.41 (m, 1H), 4.24 (s, 2H), 3.92~3.69 (m, 7H), 3.02~2.73 (m, 4H).

EXAMPLE 21

Synthesis of 4'-demethyl-4'-O-allylcarbamoyl-1-deoxypodophyllotoxin (1b-7)

The same procedure as Example 15 was carried out except that allylisocyanate (83 mg, 1 mmol) was used to give 160 mg of the title compound.

Yield: 34%.

$^1$H-NMR (ppm): d 6.64 (s, 1H), 6.52 (s, 1H), 6.36 (s, 2H), 5.91~5.80 (m, 3H), 4.91 (br, 1H, —NH), 5.32 (d, J=16.5 Hz, 1H), 5.21 (d, J=9.2 Hz, 1H), 4.61 (s, 1H), 4.40 (m, 1H), 3.92~3.59 (m, 9H), 3.00~2.77 (m, 4H).

EXAMPLE 22

Synthesis of 4'-demethyl-4'-O-phenylcarbamoyl-1-deoxypodophyllotoxin (1b-8)

The same procedure as Example 15 was carried out except that phenylisocyanate (119 mg, 1 mmol) was used to give 440 mg of the title compound.

Yield: 88%.

$^1$H-NMR (ppm): d 6.96~7.60 (m, 5H), 6.65 (s, 1H), 6.52 (s, 1H), 6.38 (s, 2H), 5.93 (s, 2H), 5.09 (br, 1H, —NH), 4.59 (s, 1H), 4.40 (m, 1H), 3.93~3.71 (m, 7H), 3.01~2.73 (m, 4H).

EXAMPLE 23

Synthesis of 4'-demethyl-4'-O-(4-fluorophenylcarbamoyl)-1-deoxypodophyllo-toxin (1b-9)

The same procedure as Example 15 was carried out except that 4-fluorophenylisocyanate (137 mg, 1 mmol) was used to give 450 mg of the title compound.

Yield: 87%

$^1$H-NMR (ppm): d 7.58 (d, J=9.12 Hz, 2H), 6.91 (d, J=9.12 Hz, 2H), 6.64 (s, 1H), 6.51 (s, 1H), 6.39 (s, 2H), 5.92 (s, 2H), 5.06 (br, 1H, —NH), 4.58 (s, 1H), 4.43 (m, 1H), 3.91-3.70 (m, 7H), 3.03~2.77 (m, 4H).

EXAMPLE 24

Synthesis of 4'-demethyl-4'-O-(4-methoxyphenylcarbamoyl)-1-deoxypodophyllotoxin (1b-10)

The same procedure as Example 15 was carried out except that 4-methoxyphenylisocyanate (149 mg, 1 mmol) was used to give 450 mg of the title compound.

Yield: 85%.

$^1$H-NMR (ppm): d 6.79 (d, J=9.32 Hz, 2H), 6.65 (s, 1H), 6.56 (d, J=9.32 Hz, 2H), 6.52 (s, 1H), 6.38 (s, 2H), 5.93 (s, 2H), 5.09 (br, 1H, —NH), 4.52 (s, 1H), 4.43 (m, 1H), 3.98~3.73 (m, 10H), 3.01~2.77 (m, 4H).

EXAMPLE 25

Synthesis of 4'-demethyl-4'-O-(4-methylphenylcarbamoyl)-1-deoxypodophyllotoxin (1b-11)

The same procedure as Example 15 was carried out except that 4-methylphenylisocyanate (133 mg, 1 mmol) was used to give 410 mg of the title compound.

Yield: 80%.

$^1$H-NMR (ppm): d 6.93 (d, J=9.19 Hz, 2H), 6.64 (s, 1H), 6.56 (d, J=9.19 Hz, 2H), 6.51 (s, 1H), 6.39 (s, 2H), 5.92 (s, 2H), 5.11 (br, 1H, —NH), 4.50 (s, 1H), 4.40 (m, 1H), 3.93~3.71 (m, 7H), 3.03~2.78 (m, 4H), 2.31 (s, 3H).

EXAMPLE 26

Synthesis of 4'-demethyl-4'-O-(4-methylthiophenylcarbamoyl)-1-deoxypodophyllotoxin (1b-12)

The same procedure as Example 15 was carried out except that 4-methylthiophenylisocyanate (165 mg, 1 mmol) was used to give 430 mg of the title compound.

Yield: 78%.

$^1$H-NMR (ppm): d 7.13 (d, J=9.23 Hz, 2H), 6.66 (s, 1H), 6.57 (d, J=9.23 Hz, 2H), 6.51 (s, 1H), 6.37 (s, 2H), 5.92 (s, 2H), 5.13 (br, 1H, —NH), 4.49 (s, 1H), 4.39 (m, 1H), 3.91~3.69 (m, 7H), 3.03~2.79 (m, 4H), 2.4 (s, 3H).

EXAMPLE 27

Synthesis of 4'-demethyl-4'-O-(2-methoxyphenylcarbamoyl)-1-deoxypodophyllotoxin (1b-13)

The same procedure as Example 15 was carried out except that 2-methoxyphenylisocyanate (149 mg, 1 mmol) was used to give 460 mg of the title compound.

Yield: 87%.

$^1$H-NMR (ppm): d 6.6~6.8 (m, 5H), 6.64 (s, 1H), 6.52 (s, 1H), 6.39 (s, 2H), 5.92 (s, 2H), 5.10 (br, 1H, —NH), 4.51 (s, 1H), 4.41 (m, 1H), 3.91~3.71 (m, 7H), 2.99~2.76 (m, 4H).

EXAMPLE 28

Synthesis of 4'-demethyl-4'-O-benzylcarbamoyl-1-deoxypodophyllotoxin (1b-14)

The same procedure as Example 15 was carried out except that benzylisocyanate (133 mg, 1 mmol) was used to give 410 mg of the title compound.

Yield: 80%.

¹H-NMR (ppm): d 7.14~7.02 (m, 5H), 6.65 (s, 1H), 6.52 (s, 1H), 6.39 (s, 2H), 5.93 (s, 2H), 5.11 (br, 1H, —NH), 4.52 (s, 1H), 4.41 (m, 1H), 4.22 (s, 2H), 3.92~3.71 (m, 7H), 3.01~2.76 (m, 4H).

EXAMPLE 29

Synthesis of 4'-demethyl-4'-O-benzoylcarbamoyl-1-deoxypodophyllotoxin (1b-15)

The same procedure as Example 15 was carried out except that benzoylisocyanate (147 mg, 1 mmol) was used to give 380 mg of the title compound.

Yield: 71%.

¹H-NMR (ppm): d 7.95~7.44 (m, 5H), 6.66 (s, 1H), 6.52 (s, 1H), 6.37 (s, 2H), 5.91 (s, 2H), 4.52 (s, 1H), 4.40 (m, 1H), 3.91~3.73 (m, 7H), 3.02~2.77 (m, 4H).

EXAMPLE 30

Synthesis of 4'-demethyl-4'-O-benzenesulfonylcarbamoyl-1-deoxypodophyllo-toxin (1b-16)

The same procedure as Example 15 was carried out except that benzenesulfonylisocyanate (183 mg, 1 mmol) was used to give 306 mg of the title compound.

Yield: 54%.

¹H-NMR (ppm): d 7.93~7.30 (m, 5H), 6.65 (s, 1H), 6.52 (s, 1H), 6.37 (s, 2H), 5.93 (s, 2H), 4.50 (s, 1H), 4.41 (m, 1H), 3.92~3.73 (m, 7H), 3.00~2.77 (m, 4H).

EXAMPLE 31

Synthesis of 4'-demethyl-4'-O-(3,4,5-trimethoxyphenylcinnamoyl)-1-deoxypodophyllotoxin (1c-1)

To a 50 ml round-bottomed flask were introduced 4'-demethyldeoxypodophyllotoxin (384 mg, 1 mmol), dicyclohexylcarbodiimide (206 mg, 1 mmol), and 4-dimethylaminopyridine (61.1 mg, 0.5 mmol), which was then dissolved in anhydrous dichloromethane (20 ml). 3,4,5-trimethoxycinnamic acid (238 mg, 1 mmol) was added thereto under 4° C. and nitrogen gas and the mixture was stirred for 1 hour. To the reaction mixture was added distilled water (100 ml). The resulting mixture was extracted three times with dichloromethane (80 ml). The extracts were combined, dried over anhydrous sodium sulfate, and concentrated under reduced pressure. The resulting crude product was purified by silica gel column (1×'5 cm) (eluent: cyclohexane:ethyl acetate-3:1, v/v) to give 540 mg of the title compound.

Yield: 89%.

¹H-NMR (ppm): d 7.77 (d, J=15.7 Hz, 1H), 6.81 (s, 2H), 6.67 (s, 1H), 6.61 (d, J=15.7 Hz, 1H), 6.55 (s, 1H), 6.42 (s, 2H), 5.95 (s, 2H), 4.66 (s, 1H), 4.50 (m, 1H), 4.16~3.99 (m, 1H), 3.83 (s, 9H), 3.66 (s, 6H), 3.08~2.74 (m, 4H).

EXAMPLE 32

Synthesis of 4'-demethyl-4'-O-(4-dimethylaminophenylacetyl)-1-deoxypodophyllotoxin (1c-2)

The same procedure as Example 31 was carried out except that 4-dimethylaminophenylacetic acid (179 mg, 1 mmol) was used to give 425 mg of the title compound.

Yield: 80%.

¹H-NMR (ppm): d 7.28 (d, J=8.77 Hz, 2H), 7.08 (d, J=8.77 Hz, 2H), 6.66 (s, 1H), 6.51 (s, 1H), 6.36 (s, 2H), 5.94 (s, 2H), 5.09 (br, 1H, —NH), 4.63 (s, 1H), 4.46 (m, 1H), 3.90~3.81 (m, 3H), 3.66 (s, 3H), 3.64 (s, 3H), 3.19~2.68 (m, 10H).

EXAMPLE 33

Synthesis of 4'-demethyl-4'-O-acetyl-1-deoxypodophyllotoxin (1c-3)

To a 50 ml round-bottomed flask were introduced 4'-demethyldeoxypodophyllotoxin (384 mg, 1 mmol), dicyclohexylcarbodiimide (247 mg, 1.2 mmol), 4-dimethylaminopyridine (49 mg, 0.4 mmol), and acetic acid (72 mg, 1.2 mmol), which was then dissolved in anhydrous dichloromethane (20 ml). The resulting mixture was stirred at 0° C. for 2 hours. The reaction mixture was filtered and distilled water (100 ml) was added thereto. The resulting mixture was extracted three times with dichloromethane (100 ml). The extracts were combined, dried over anhydrous sodium sulfate, and concentrated under reduced pressure. The resulting crude product was purified by silica gel column (1×'15 cm) (eluent: cyclohexane:ethyl acetate= 4:1, v/v) to give 362 mg of the title compound.

Yield: 85%.

¹H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.29 (s, 3H).

EXAMPLE 34

Synthesis of 4'-demethyl-4'-O-propanoyl-1-deoxypodophyllotoxin (1c-4)

The same procedure as Example 33 was carried out except that propionic acid (89 mg, 1.2 mmol) was used to give 365 mg of the title compound.

Yield: 83%.

¹H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.29 (s, q, J=7.65 Hz, 2H), 1.24 (t, J=7.65 Hz, 3H).

EXAMPLE 35

Synthesis of 4'-demethyl-4'-O-butanoyl-1-deoxypodophyllotoxin (1c-5)

The same procedure as Example 33 was carried out except that butyric acid (106 mg, 1.2 mmol) was used to give 409 mg of the title compound.

Yield: 90%.

¹H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.55 (s, t, J=7.38 Hz, 2H), 1.77 (m, 2H), 1.02 (t, J=7.38 Hz, 3H).

EXAMPLE 36

Synthesis of 4'-demethyl-4'-O-(3'-methylbutanoyl)-1-deoxypodophyllotoxin (1c-6)

The same procedure as Example 33 was carried out except that 3'-methylbutanoic acid (122 mg, 1.2 mmol) was used to give 412 mg of the title compound.

Yield: 88%.

$^1$H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.24 (d, J=5.67 Hz, 2H), 2.10~2.22 (m, 1H), 1.06 (s, 3H), 0.99 (s, 3H).

EXAMPLE 37

Synthesis of 4'-demethyl-4'-O-heptanoyl-1-deoxypodophyllotoxin (1c-7)

The same procedure as Example 33 was carried out except that heptanoic acid (156 mg, 1.2 mmol) was used to give 456 mg of the title compound.

Yield: 92%.

$^1$H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.55 (t, J=7.1 Hz, 2H), 1.55~1.72 (m, 2H), 1.30 (s, br, 4H), 0.88 (t, J=5.94 Hz, 3H).

EXAMPLE 38

Synthesis of 4'-demethyl-4'-O-octanoyl-1-deoxypodophyllotoxin (1c-8)

The same procedure as Example 33 was carried out except that octanoic acid (173 mg, 1.2 mmol) was used to give 434 mg of the title compound.

Yield: 85%.

$^1$H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.56 (t, J=7.38 Hz, 2H), 1.56~1.73 (m, 2H), 1.30 (s, br, 8H), 0.87 (t, J=3.42 Hz, 3H).

EXAMPLE 39

Synthesis of 4'-demethyl-4'-O-decanoyl-1-deoxypodophyllotoxin (1c-9)

The same procedure as Example 33 was carried out except that decanoic acid (206 mg, 1.2 mmol) was used to give 468 mg of the title compound.

Yield: 87%.

$^1$H-NMR (ppm): d 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.56 (t, J=7.3 Hz, 2H), 1.55~1.72 (m, 2H), 1.23 (s, br, 12H), 0.92 (t, J=5.4 Hz, 3H).

EXAMPLE 40

Synthesis of 4'-demethyl-4'-O-benzoyl-1-deoxypodophyllotoxin (1c-10)

The same procedure as Example 33 was carried out except that benzoic acid (146 mg, 1.2 mmol) was used to give 405 mg of the title compound.

Yield: 83%.

$^1$H-NMR (ppm): d 8.15 (d, J=8.1 Hz, 2H), 7.4~7.6 (m, 3H), 6.65 (s, 1H), 6.49 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H).

EXAMPLE 41

Synthesis of 4'-demethyl-4'-O-dodecanoyl-1-deoxypodophyllotoxin (1c-11)

The same procedure as Example 33 was carried out except that dodecanoic acid (240 mg, 1.2 mmol) was used to give 515 mg of the title compound.

Yield: 91%.

$^1$H-NMR (ppm): d 6.65 (s, 1H), 6.51 (s, 1H), 6.37 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.56 (t, J=7.3 Hz, 2H), 1.55~1.72 (m, 2H), 1.23 (s, br, 12H), 0.88 (t, J=5.4 Hz, 3H).

EXAMPLE 42

Synthesis of 4'-demethyl-4'-O-tetradecanoyl-1-deoxypodophyllotoxin (1c-12)

The same procedure as Example 33 was carried out except that tetradecanoic acid (273 mg, 1.2 mmol) was used to give 594 mg of the title compound.

Yield: 90%.

$^1$H-NMR (ppm): d 6.66 (s, 1H), 6.53 (s, 1H), 6.38 (s, 2H), 5.91 (s, br, 2H), 4.61 (s, br, 1H), 4.56~4.32 (m, 1H), 3.72~4.04 (m, 1H), 3.66 (s, 6H), 3.22~2.54 (m, 4H), 2.56 (t, J=7.3 Hz, 2H), 1.55~1.72 (m, 2H), 1.25 (s, br, 20H), 0.88 (t, J=5.4 Hz, 3H).

EXAMPLE 43

Synthesis of 4'-demethyl-4'-O-hexadecanoyl-1-deoxypodophyllotoxin (1c-13)

The same procedure as Example 33 was carried out except that hexadecanoic acid (307 mg, 1.2 mmol) was used to give 529 mg of the title compound.

Yield: 85%.

$^1$H-NMR (ppm): d 6.63 (s, 1H), 6.50 (s, 1H), 6.37 (s, 2H), 5.91 (s, br, 2H), 4.61 (s, br, 1H), 4.56~4.32 (m, 1H), 3.72~4.04 (m, 1H), 3.67 (s, 6H), 3.22~2.54 (m, 4H), 2.56 (t, J=7.3 Hz, 2H), 1.55~1.72 (m, 2H), 1.25 (s, br, 24H), 0.87 (t, J=5.4 Hz, 3H).

EXAMPLE 44

Synthesis of 4'-demethyl-4'-O-(cis-9'-hexadecenoyl)-1-deoxypodophyllo-toxin (1c-14)

The same procedure as Example 33 was carried out except that cis-9'-hexadecenoic acid (304 mg, 1.2 mmol) was used to give 508 mg of the title compound.

Yield: 82%.

$^1$H-NMR (ppm): d 6.63 (s, 1H), 6.50 (s, 1H), 6.37 (s, 2H), 5.91 (s, br, 2H), 5.28 (m, 2H), 4.61 (s, br, 1H), 4.56~4.32 (m, 1H), 3.72~4.04 (m, 1H), 3.67 (s, 6H), 3.22~2.54 (m, 4H), 2.56 (t, J=7.3 Hz, 2H), 1.99 (s, br, 4H), 1.55~1.72 (m, 2H), 1.30 (s, br, 18H), 0.87 (t, J=5.4 Hz, 3H).

EXAMPLE 45

Synthesis of 4'-demethyl-4'-O-octadecanoyl-1-deoxypodophyllotoxin (1c-15)

The same procedure as Example 33 was carried out except that octadecanoic acid (341 mg, 1.2 mmol) was used to give 507 mg of the title compound.

Yield: 78%.

$^1$H-NMR (ppm): d 6.66 (s, 1H), 6.52 (s, 1H), 6.37 (s, 2H), 5.91 (s, br, 2H), 4.61 (s, br, 1H), 4.56~4.32 (m, 1H), 3.72~4.04 (m, 1H), 3.68 (s, 6H), 3.22~2.54 (m, 4H), 2.57 (t, J=7.3 Hz, 2H), 1.55~1.72 (m, 2H), 1.25 (s, br, 28H), 0.87 (t, J=5.4 Hz, 3H).

EXAMPLE 46

Synthesis of 4'-demethyl-4'-O-(cis-9'-octadecenoyl)-1-deoxypodophyllo-toxin (1c-16)

The same procedure as Example 33 was carried out except that cis-9'-octadecenoic acid (339 mg, 1.2 mmol) was used to give 512 mg of the title compound.

Yield: 79%.
$^1$H-NMR (ppm): d 6.65 (s, 1H), 6.51 (s, 1H), 6.38 (s, 2H), 5.34 (t, J=4.68 Hz, 2H), 4.61 (s, br, 1H), 4.56~4.32 (m, 1H), 3.72~4.04 (m, 1H), 3.68 (s, 6H), 3.22~2.54 (m, 4H), 2.56 (t, J=7.3 Hz, 2H), 1.98 (s, br, 4H), 1.55~1.72 (m, 2H), 1.27 (s, br, 20H), 0.87 (t, J=5.4 Hz, 3H).

EXAMPLE 47

Synthesis of 4'-demethyl-4'-O-(trans-9'-octadecenoyl)-1-deoxypodophyllo-toxin (1c-17)

The same procedure as Example 33 was carried out except that trans-9'-octadecenoic acid (339 mg, 1.2 mmol) was used to give 486 mg of the title compound.
Yield: 75%.
$^1$H-NMR (ppm): d 6.65 (s, 1H), 6.51 (s, 1H), 6.37 (s, 2H), 5.91 (s, br, 2H), 5.30~5.45 (m, 2H), 4.61 (s, br, 1H), 4.56~4.32 (m, 1H), 3.72~4.04 (m, 1H), 3.67 (s, 6H), 3.22-2.54 (m, 4H), 2.56 (t, J=7.3 Hz, 2H), 1.98 (s, br, 4H), 1.55~1.72 (m, 2H), 1.26 (s, br, 20H), 0.87 (t, J=5.4 Hz, 3H).

EXAMPLE 48

Synthesis of 4'-demethyl-4'-O-(cis-11'-octadecenoyl)-1-deoxypodophyllo-toxin (1c-18)

The same procedure as Example 33 was carried out except that cis-11'-octadecenoic acid (339 mg, 1.2 mmol) was used to give 473 mg of the title compound.
Yield: 73%.
$^1$H-NMR (ppm): d 6.65 (s, 1H), 6.51 (s, 1H), 6.38 (s, 2H), 5.91 (s, br, 2H), 5.34 (t, J=4.68, 2H), 4.61 (s, br, 1H), 4.56~4.32 (m, 1H), 3.72~4.04 (m, 1H), 3.68 (s, 6H), 3.22~2.54 (m, 4H), 2.56 (t, J=7.3 Hz, 2H), 1.98 (s, br, 4H), 1.55~1.72 (m, 2H), 1.27 (s, br, 20H), 0.87 (t, J=5.4 Hz, 3H).

EXAMPLE 49

Synthesis of 4'-demethyl-4'-O-(trans-11'-octadecenoyl)-1-deoxypodophyllo-toxin (1c-19)

The same procedure as Example 33 was carried out except that trans-11'-octadecenoic acid (339 mg, 1.2 mmol) was used to give 492 mg of the title compound.
Yield: 76%.
$^1$H-NMR (ppm): d 6.65 (s, 1H), 6.50 (s, 1H), 6.37 (s, 2H), 5.90 (s, br, 2H), 5.30~5.45 (m, 2H), 4.61 (s, br, 1H), 4.56~4.32 (m, 1H), 3.72~4.04 (m, 1H), 3.67 (s, 6H), 3.22~2.54 (m, 4H), 2.56 (t, J=7.3 Hz, 2H), 1.98 (s, br, 4H), 1.55~1.72 (m, 2H), 1.26 (s, br, 20H), 0.87 (t, J=5.4 Hz, 3H).

EXAMPLE 50

Synthesis of 4'-demethyl-4'-O-(cis-9',12'-octadecadienoyl)-1-deoxypodophyllo-toxin (1c-20)

The same procedure as Example 33 was carried out except that cis-9',12'-octadecadienoic acid (336 mg, 1.2 mmol) was used to give 504 mg of the title compound.
Yield: 78%.
$^1$H-NMR (ppm): d 6.65 (s, 1H), 6.51 (s, 1H), 6.37 (s, 2H), 5.91 (s, br, 2H), 5.30~5.41 (m, 4H), 4.61 (s, br, 1H), 4.56~4.32 (m, 1H), 3.72~4.04 (m, 1H), 3.67 (s, 6H), 3.22~2.54 (m, 6H), 2.56 (t, J=7.3 Hz, 2H), 2.00~2.15 (m, 4H), 1.55~1.72 (m, 2H), 1.26 (s, br, 20H), 0.87 (t, J=5.4 Hz, 3H).

EXAMPLE 51

Synthesis of 4'-demethyl-4'-O-(trans-9',12'-octadecadienoyl)-1-deoxypodophyllo-toxin (1c-21)

The same procedure as Example 33 was carried out except that trans-9',12'-octadecadienoic acid (336 mg, 1.2 mmol) was used to give 485 mg of the title compound.

Yield: 75%.
$^1$H-NMR (ppm): d 6.66 (s, 1H), 6.52 (s, 1H), 6.38 (s, 2H), 5.92 (s, br, 2H), 5.30~5.45 (m, 4H), 4.61 (s, br, 1H), 4.56~4.32 (m, 1H), 3.72~4.04 (m, 1H), 3.68 (s, 6H), 3.02~2.54 (m, 6H), 2.56 (t, J=7.3 Hz, 2H), 2.00~2.15 (m, 4H), 1.55~1.72 (m, 2H), 1.26 (s, br, 20H), 0.88 (t, J=6.1 Hz, 3H).

EXAMPLE 52

Synthesis of 4'-demethyl-4'-O-(cis-9',12',15'-octadecatrienoyl)-1-deoxypodophyllotoxin (1c-22)

The same procedure as Example 33 was carried out except that cis-9',12',15'-octadecatrienoic acid (334 mg, 1.2 mmol) was used to give 464 mg of the title compound.
Yield: 72%.
$^1$H-NMR (ppm): d 6.65 (s, 1H), 6.50 (s, 1H), 6.36 (s, 2H), 5.91 (s, br, 2H), 5.35 (s, br, 6H), 4.62 (s, br, 1H), 4.56~4.32 (m, 1H), 3.72~4.04 (m, 1H), 3.67 (s, 6H), 3.02~2.54 (m, 8H), 2.56 (t, J=7.1 Hz, 2H), 2.00~2.15 (m, 4H), 1.55~1.72 (m, 2H), 1.26 (s, br, 20H), 0.96 (t, J=7.1 Hz, 3H).

EXAMPLE 53

Synthesis of 4'-demethyl-4'-O-(cis-6',9',12'-octadecatrienoyl)-1-deoxypodophyllotoxin (1c-23)

The same procedure as Example 33 was carried out except that cis-6',9',12'-octadecatrienoic acid (334 mg, 1.2 mmol) was used to give 451 mg of the title compound.
Yield: 70%.
$^1$H-NMR (ppm): d 6.66 (s, 1H), 6.52 (s, 1H), 6.38 (s, 2H), 5.93 (s, br, 2H), 5.25~5.39 (m, 6H), 4.62 (s, br, 1H), 4.56~4.32 (m, 1H), 3.72~4.04 (m, 1H), 3.68 (s, 6H), 3.02~2.54 (m, 8H), 2.59 (t, J=7.1 Hz, 2H), 2.00~2.15 (m, 4H), 1.55~1.72 (m, 2H), 1.26 (s, br, 10H), 0.96 (t, J=7.1 Hz, 3H).

EXAMPLE 54

Synthesis of 4'-demethyl-4'-O-eicosanoyl-1-deoxypodophyllotoxin (1c-24)

The same procedure as Example 33 was carried out except that eicosanoic acid (375 mg, 1.2 mmol) was used to give 536 mg of the title compound.
Yield: 79%.
$^1$H-NMR (ppm): d 6.64 (s, 1H), 6.50 (s, 1H), 6.38 (s, 2H), 5.90 (s, br, 2H), 4.61 (s, br, 1H), 4.56~4.32 (m, 1H), 3.72~4.04 (m, 1H), 3.67 (s, 6H), 3.22~2.54 (m, 4H), 2.56 (t, J=7.3 Hz, 2H), 1.55~1.72 (m, 2H), 1.26 (s, br, 32H), 0.87 (t, J=5.4 Hz, 3H).

EXAMPLE 55

Synthesis of 4'-demethyl-4'-O-(cis-11'-eicosenoyl)-1-deoxypodophyllotoxin (1c-25)

The same procedure as Example 33 was carried out except that cis-11'-eicosenoic acid (372 mg, 1.2 mmol) was used to give 541 mg of the title compound.
Yield: 80%.
$^1$H-NMR (ppm): d 6.65 (s, 1H), 6.51 (s, 1H), 6.37 (s, 2H), 5.92 (s, br, 2H), 5.34 (t, J=4.68 Hz, 2H), 4.63 (s, br, 1H), 4.56~4.32 (m, 1H), 3.72~4.04 (m, 1H), 3.68 (s, 6H), 3.22~2.54 (m, 4H), 2.57 (t, J=7.3 Hz, 2H), 1.95~2.05 (m, 4H), 1.55~1.72 (m, 2H), 1.29 (s, br, 28H), 0.87 (t, J=5.4 Hz, 3H).

EXAMPLE 56

Synthesis of 4'-demethyl-4'-O-(trans-11'-eicosenoyl)-1-deoxypodophyllotoxin (1c-26)

The same procedure as Example 33 was carried out except that trans-11'-eicosenoic acid (372 mg, 1.2 mmol) was used to give 561 mg of the title compound.

Yield: 83%.

$^1$H-NMR (ppm): d 6.65 (s, 1H), 6.50 (s, 1H), 6.37 (s, 2H), 5.90 (s, br, 2H), 5.30~5.45 (m, 2H), 4.61 (s, br, 1H), 4.56~4.32 (m, 1H), 3.72~4.04 (m, 1H), 3.67 (s, 6H), 3.22~2.54 (m, 6H), 2.56 (t, J=7.3 Hz, 2H), 2.00~2.15 (m, 4H), 1.55~1.72 (m, 2H), 1.26 (s, br, 24H), 0.88 (t, J=5.4 Hz, 3H).

EXAMPLE 57

Synthesis of 4'-demethyl-4'-O-(cis-11',14'-eicosadienoyl)-1-deoxypodophyllotoxin (1c-27)

The same procedure as Example 33 was carried out except that cis-11',14'-eicosadienoic acid (370 mg, 1.2 mmol) was used to give 580 mg of the title compound.

Yield: 86%.

$^1$H-NMR (ppm): d 6.65 (s, 1H), 6.51 (s, 1H), 6.37 (s, 2H), 5.91 (s, br, 2H), 5.30~5.41 (m, 4H), 4.61 (s, br, 1H), 4.56~4.32 (m, 1H), 3.72~4.04 (m, 1H), 3.67 (s, 6H), 3.22~2.54 (m, 6H), 2.56 (t, J=7.3 Hz, 2H), 2.00~2.15 (m, 4H), 1.55~1.72 (m, 2H), 1.26 (s, br, 24H), 0.88 (t, J=5.4 Hz, 3H).

EXAMPLE 58

Synthesis of 4'-demethyl-4'-O-(cis-5',8',11',14'-eicosatetraenoyl)-1-deoxypodophyllotoxin (1c-28)

The same procedure as Example 33 was carried out except that cis-5',8',11',14'-eicosatetraenoic acid (365 mg, 1.2 mmol) was used to give 590 mg of the title compound.

Yield: 88%.

$^1$H-NMR (ppm): d 6.65 (s, 1H), 6.51 (s, 1H), 6.38 (s, 2H), 5.92 (s, br, 2H), 5.2~5.6 (m, 8H), 4.63 (s, br, 1H), 4.56~4.32 (m, 1H), 3.72~4.04 (m, 1H), 3.67 (s, 6H), 3.22~2.54 (m, 10H), 2.59 (t, J=7.3 Hz, 2H), 1.95~2.25 (m, 4H), 1.55~1.72 (m, 2H), 1.29 (s, br, 28H), 0.88 (t, J=5.4 Hz, 3H).

EXAMPLE 59

Synthesis of 4'-demethyl-4'-O-docosanoyl-1-deoxypodophyllotoxin (1c-29)

The same procedure as Example 33 was carried out except that docosanoic acid (408 mg, 1.2 mmol) was used to give 558 mg of the title compound.

Yield: 79%.

$^1$H-NMR (ppm): d 6.66 (s, 1H), 6.52 (s, 1H), 6.38 (s, 2H), 5.93 (s, br, 2H), 4.61 (s, br, 1H), 4.56~4.32 (m, 1H), 3.72~4.04 (m, 1H), 3.68 (s, 6H), 3.22~2.54 (m, 4H), 2.57 (t, J=7.3 Hz, 2H), 1.55~1.72 (m, 2H), 1.00~1.4 (m, 36H), 0.88 (t, J=5.4 Hz, 3H).

EXAMPLE 60

Synthesis of 4'-demethyl-4'-O-(cis-13'-docosenoyl)-1-deoxypodophyllotoxin (1c-30)

The same procedure as Example 33 was carried out except that cis-13'-docosenoic acid (408 mg, 1.2 mmol) was used to give 530 mg of the title compound.

Yield: 75%.

$^1$H-NMR (ppm): d 6.65 (s, 1H), 6.51 (s, 1H), 6.37 (s, 2H), 5.92 (s, br, 2H), 5.34 (t, J=4.68 Hz, 2H), 4.63 (s, br, 1H), 4.56~4.32 (m, 1H), 3.72~4.04 (m, 1H), 3.68 (s, 6H), 3.22~2.54 (m, 4H), 2.57 (t, J=7.3 Hz, 2H), 1.95~2.05 (m, 4H), 1.55~1.72 (m, 2H), 1.29 (s, br, 32H), 0.87 (t, J=5.4 Hz, 3H).

EXAMPLE 61

Synthesis of 4'-demethyl-4'-O-(cis-4',7',10',13',16',19'-docohexaenoyl)-1-deoxypodophyllotoxin (1c-31)

The same procedure as Example 33 was carried out except that cis-4',7',10',13',16',19'-docohexaenoic acid (396 mg, 1.2 mmol) was used to give 633 mg of the title compound.

Yield: 91%.

$^1$H-NMR (ppm): d 6.67 (s, 1H), 6.53 (s, 1H), 6.38 (s, 2H), 5.93 (s, br, 2H), 5.28~5.6 (m, 12H), 4.63 (s, br, 1H), 4.56~4.32 (m, 1H), 3.72~4.04 (m, 1H), 3.67 (s, 6H), 3.22~2.54 (m, 14H), 2.4~2.6 (m, 2H), 2.0~2.2 (m, 2H), 1.80~2.00 (m, 2H), 0.97 (t, J=7.1 Hz, 3H).

EXAMPLE 62

Synthesis of 4'-demethyl-4'-O-retinoyl-1-deoxypodophyllotoxin (1c-32)

The same procedure as Example 33 was carried out except that retinoic acid (360 mg, 1.2 mmol) was used to give 500 mg of the title compound.

Yield: 75%.

$^1$H-NMR (ppm): d 6.8~7.05 (m, 1H), 6.66 (s, 1H), 6.53 (s, 1H), 6.40 (s, 2H), 6.1~6.45 (m, 5H), 5.92 (s, br, 2H), 4.63 (s, br, 1H), 4.56~4.32 (m, 1H), 3.72~4.04 (m, 1H), 3.69 (s, 6H), 3.02~2.5 (m, 4H), 2.38 (s, 3H), 2.01 (s, br, 5H), 1.72 (s, 3H), 1.4~1.6 (m, 2H), 1.26 (s, br, 2H), 1.03 (s, 6H).

EXAMPLE 63

Synthesis of 4'-demethyl-4'-O-(5'-carboxy-pentanoyl)-1-deoxypodophyllotoxin (1c-33)

The same procedure as Example 33 was carried out except that adipic acid (480 mg, 3.6 mmol) was used to give 368 mg of the title compound.

Yield: 70%.

$^1$H-NMR (ppm): d 6.65 (s, 1H), 6.51 (s, 1H), 6.36 (s, 2H), 5.93 (s, br, 2H), 4.63 (s, br, 1H), 4.56~4.32 (m, 1H), 3.72~4.04 (m, 1H), 3.67 (s, 6H), 3.02~2.5 (m, 6H), 2.3~2.5 (m, 2H), 1.7~1.9 (m, 4H).

EXAMPLE 64

Synthesis of 4'-demethyl-4'-O-(7'-carboxy-heptanoyl)-1-deoxypodophyllotoxin (1c-34)

The same procedure as Example 33 was carried out except that suberic acid (626 mg, 3.6 mmol) was used to give 351 mg of the title compound.

Yield: 65%.

$^1$H-NMR (ppm): d 6.65 (s, 1H), 6.50 (s, 1H), 6.36 (s, 2H), 5.92 (s, br, 2H), 4.59 (s, br, 1H), 4.56~4.32 (m, 1H), 3.72~4.04 (m, 1H), 3.67 (s, 6H), 3.02~2.5 (m, 4H), 2.56 (t, J=7.1 Hz, 2H), 2.33 (t, J=7.1 Hz, 2H), 1.55~1.8 (m, 2H), 1.31 (s, br, 8H).

EXAMPLE 65

Synthesis of 4'-demethyl-4'-O-(9'-carboxy-nonanoyl)-1-deoxypodophyllotoxin (1c-35)

The same procedure as Example 33 was carried out except that sebacic acid (727 mg, 3.6 mmol) was used to give 358 mg of the title compound.

Yield: 63%.

$^1$H-NMR (ppm): d 6.65 (s, 1H), 6.51 (s, 1H), 6.36 (s, 2H), 5.92 (s, br, 2H), 4.59 (s, br, 1H), 4.56~4.32 (m, 1H), 3.72~4.04 (m, 1H), 3.67 (s, 6H), 3.02~2.5 (m, 4H), 2.56 (t, J=7.1 Hz, 2H), 2.33 (t, J=7.1 Hz, 2H), 1.55~1.8 (m, 2H), 1.31 (s, br, 12H).

EXAMPLE 66

Synthesis of 4'-demethyl-4'-O-(11'-carboxy-undecanoyl)-1-deoxypodophyllotoxin (1c-36)

The same procedure as Example 33 was carried out except that dodecandioic acid (828 mg, 3.6 mmol) was used to give 370 mg of the title compound.

Yield: 62%.

$^1$H-NMR (ppm): d 6.66 (s, 1H), 6.52 (s, 1H), 6.37 (s, 2H), 5.92 (s, br, 2H), 4.60 (s, br, 1H), 4.56~4.32 (m, 1H), 3.72~4.04 (m, 1H), 3.66 (s, 6H), 3.02~2.5 (m, 4H), 2.57 (t, J=7.1 Hz, 2H), 2.34 (t, J=7.1 Hz, 2H), 1.55~1.8 (m, 2H), 1.31 (s, br, 16H).

EXAMPLE 67

Synthesis of 4'-demethyl-4'-O-(13'-carboxy-tridecanoyl)-1-deoxypodophyllotoxin (1c-37)

The same procedure as Example 33 was carried out except that tetradecandioic acid (929 mg, 3.6 mmol) was used to give 374 mg of the title compound.

Yield: 60%.

$^1$H-NMR (ppm): d 6.66 (s, 1H), 6.52 (s, 1H), 6.38 (s, 2H), 5.93 (s, br, 2H), 4.60 (s, br, 1H), 4.56~4.32 (m, 1H), 3.72~4.04 (m, 1H), 3.69 (s, 6H), 3.02~2.5 (m, 4H), 2.57 (t, J=7.1 Hz, 2H), 2.34 (t, J=7.1 Hz, 2H), 1.55~1.8 (m, 2H), 1.31 (s, br, 20H).

EXAMPLE 68

Synthesis of 4'-demethyl-4'-O-(15'-carboxy-pentadecanoyl)-1-deoxypodophyllotoxin (1c-38)

The same procedure as Example 33 was carried out except that hexadecandioic acid (1030 mg, 3.6 mmol) was used to give 411 mg of the title compound.

Yield: 63%.

$^1$H-NMR (ppm): d 6.66 (s, 1H), 6.52 (s, 1H), 6.37 (s, 2H), 5.93 (s, br, 2H), 4.63 (s, br, 1H), 4.56~4.32 (m, 1H), 3.72~4.04 (m, 1H), 3.68 (s, 6H), 3.02~2.5 (m, 4H), 2.57 (t, J=7.1 Hz, 2H), 2.33 (t, J=7.1 Hz, 2H), 1.55~1.8 (m, 2H), 1.31 (s, br, 24H).

Experiment 1

Cytotoxicity Test for A549 and SK-MEL-2 Cells

Human lung carcinomas A549 and SK-MEL-2 were used for determining cytotoxicity of the compounds of the present invention according to the Sulfrhodamine-B (SRB) method which was developed by NCI in 1989 in order to determine in vitro anticancer activity of drugs.

Cells to be used in the experiment were separated from a surface using 0.5% Trypsin-EDTA solution and suspended in a density of $5 \times 10^4$ cell/ml therein. The cell suspension was introduced into a 96-well plate in an amount of 180/well and incubated for 24 hours in a 5% $CO_2$ incubator of 37° C. Samples were dissolved in dimethylsulfoxide and then diluted by water distilled in advance for three times just before the experiment. Forty-one (41) samples were prepared into 4 types of final concentrations, i.e., 0.1, 0.03, 0.01 and 0.003 mg per ml of the medium. The diluted sample solutions were added to the 96-well plate in the amount of 20 μl/well and incubated for 48 hours in a $CO_2$ incubator of 37° C. At the time of adding the samples, Tz (Time zero) plate was taken. The medium was removed from the Tz plate and each of the plates after incubation were completed. Ten (10)% trifluoroacetic acid (TCA) was added in the amount of 50 ml/well, and allowed to stand for 1 hour at 4° C. to fix the cells on the bottom surface of the plate. After the cells were fixed, the plate was washed five to six times with water to completely remove the remaining TCA solution and then dried at room temperature to completely remove the moisture. To the fully dried plate was introduced a dye solution in the amount of 50 ml/well in which 0.4% SRB was dissolved in 1% acetic acid solution. The cells were dyed for 30 minutes and washed five to six times with 1% acetic acid solution to remove SRB which did not adhere to the cells. After the dyeing process, the plate was dried again at room temperature. 100 ml of 10 mM Tris solution was added thereto in order to dissolve the dye, and then O.D. (optical density) was determined by microplate reader at 520 nm.

$ED_{50}$ values for cancer cells were calculated as follows. The amount of SRB protein was analyzed at the time when incubation started by the addition of the sample. This amount was named time zero (Tz). The O.D. value obtained from a group which was not treated by the sample was named Control group (C) and the O.D. value obtained from a group which was treated by the sample was named Test group (T).

The degree of cytotoxicity of the compounds was calculated from Tz, C and T values according to the following equation.

That is, in the case of Tz≧T, the degree was calculated by $(T-Tz)/(C-Tz) \times 100 (\%)$, and in the case of Tz<T, the degree was calculated by $(T-Tz)/Tz \times 100 (\%)$.

From the values thus obtained, $ED_{50}$ value which is defined as the concentration at which growth of the cancer cell is inhibited by 50% was calculated using the regression function of Excel program. The following Table 1 shows the test result of the compounds of formulae (1a) and (1b) for A549 cell, and Table 2 shows the test result of the compounds of formula (1c) for A549 and SK-MEL-2 cells.

Experiment 2

Anti-Cancer Test for BDF1 Mouse Transplanted by Lewis Lung Cancer Cell (LLC)

In order to evaluate the anti-cancer activity of the compounds of the present invention, LLC, which is a lung cancer cell of mouse, was transplanted into the hypodermic region of BDF1 mouse to induce a solid cancer. Test compounds were peritoneally injected hereto and the suppression degree in the size of the solid cancer was observed. Experiment for the compounds of formulae (1a) and (1b) and that for the compound of formula (1c) were separately carried out.

Experiment 2-1 [Compounds of Formulae (1a) and (1b)]

Male BDF1 mouse (Weight 18 to 25 g), being in good health and purchased from Korea Biolink Co., was used as a test animal.

The mice were bred at a place controlled to the temperature of 23 to 24° C. while provided with water and feed ad libitum. As the feed, feed for mouse containing no antibiotics was used. The hypodermic tissue of C57BL/6 mouse, which includes cells cultured therein for 14 days, was taken up. Sterilized cold physiological saline was added to the tissue in the amount of 5 ml/g tissue to make a cell suspension. This cell suspension of 0.2 ml was transplanted into the hypodermic region of armpit of BDF1 mouse.

Each group includes 5 mice. After 24 hours from the transplantation, each test compound of formulae (1a) and (1b) was dissolved in 4% Tween 80 and injected peritoneally in the amount of 0.2 ml and in a concentration of 0.06 mmole/kg/day (that is, 0.06 mmole of each test compound was dissolved in 10 ml of 4% Tween 80, and then 0.2 ml of the resulting solution was peritoneally injected into a mouse). Only 4% Tween 80 was injected for the negative control group, and the same moles of etoposide (36 mg/kg) was injected for the positive control group. The injection was performed five times at 1, 2, 4, 7 and 8 days from the transplantation of cancer.

The anti-cancer effect was determined by measuring the volume of cancer of the control and test groups at 14 to 16 days from the administration of drugs and then calculated as follows.

Volume of Cancer(mm$^3$)=Length(mm)×Width$^2$(mm$^2$)/2

Suppression Rate of Cancer Growth(%)=$(C-T)$×100(%)/$C$ in which
C represents the average volume of cancer (mm$^3$) of the control group, and
T represents the average volume of cancer (mm$^3$) of the test group.
The results are shown in the following Table 1.

Experiment 2-2 [Compound of Formula (1c)]

The compound of formula (1c) was divided into organic acid ester (formula 1c-3~13, 15, 24, 29), unsaturated fatty acid (C-18) ester (formula 1c-16~23), unsaturated fatty acid (C-16, 20 or 22) ester (formula 1c-14, 25~28, 31), and dicarboxylic acid ester (formula 1c-33~38) of DDPT.

The mice used in the experiment and transplantation of LLC cell were the same as the above Experiment 2-1.

Each group includes 5 mice. After 24 hours from the transplantation, the compound of formula (1c) was dissolved in a dissolution aid containing 5% DMSO, 20% Tween 80 and 75% physiological saline. A predetermined amount thereof was peritoneally injected after 24 hours from the transplantation (d1=day 1). Then, the time for administration was controlled by observing the weight change of the mouse. The amount of and time for administration of each compound were shown in Table 3a~3d. Only 0.2 ml of the dissolution aid was injected for the negative control group, and etoposide (36 mg/kg) was injected for the positive control group three times (d1, d5, and d9). The anti-cancer effect was determined by measuring the volume of cancer of the control and test groups at 11 to 14 days from the administration of drugs and then calculated according to the same method as Experiment 2-1.

The results are shown in the following Tables 3a~3d.

TABLE 1

Cytotoxicity for A549 cell and anti-cancer effect for mouse of the compounds of formulae (1a) and (1b)

| Com. No. | ED50(nM) for A549 | Suppression Rate for LLC |
|---|---|---|
| 1a-1 | 21.9 | — |
| 1a-2 | 68 | 88 |
| 1a-3 | 88.2 | — |
| 1a-4 | 102 | — |
| 1a-5 | 55 | — |
| 1a-7 | 86.6 | — |
| 1a-9 | 104 | — |
| 1a-10 | 96.7 | 78 |
| 1a-11 | 91.6 | 82 |
| 1a-12 | 90.3 | 82 |
| 1a-13 | 88.5 | 85.5 |
| 1a-14 | 79.6 | 90 |
| 1a-15 | 74.2 | 34.5 |
| 1a-16 | 114 | — |
| 1b-1 | 132 | — |
| 1b-2 | 153 | 90.1 |
| 1b-3 | 92 | 75 |
| 1b-4 | 163 | 88 |
| 1b-5 | 61.5 | 95.1 |
| 1b-6 | 80.3 | — |
| 1b-7 | 90.5 | — |
| 1b-8 | 177 | — |
| 1b-9 | 86.3 | — |
| 1b-10 | 95.6 | — |
| 1b-11 | 99.3 | — |
| 1b-12 | 106 | — |
| 1b-13 | 66.2 | — |
| 1b-14 | 72 | — |
| 1b-15 | 77 | — |
| 1b-16 | 50.6 | — |
| DPT | 75.5 | 60.2 |
| Etoposide | 1988.1 | 90.8 |

—: not tested
A549: Human lung cancer cell
LLC: Mouse lung cancer cell

TABLE 2

Cytotoxicity for A549 and SK-MEL-2 cells of the compound of formulae (1c)

| Com. No. | ED50(mg/mL) for A549 | ED50(mg/mL) for SK-MEL-2 |
|---|---|---|
| 1c-1 | 108(nM) | — |
| 1c-2 | 106.4(nM) | — |
| 1c-3 | 0.003 | 0.006 |
| 1c-4 | 0.004 | 0.010 |
| 1c-5 | 0.005 | 0.017 |
| 1c-6 | 0.006 | 0.089 |
| 1c-7 | 0.013 | 0.078 |
| 1c-8 | 0.009 | 0.030 |
| 1c-9 | 0.027 | 0.004 |
| 1c-10 | 0.095 | 0.066 |
| 1c-11 | 0.030 | 0.025 |
| 1c-12 | 0.041 | 0.050 |
| 1c-13 | 0.268 | 0.290 |
| 1c-14 | 0.733 | 0.065 |
| 1c-15 | 2.670 | >5 |
| 1c-16 | 0.179 | 0.159 |
| 1c-17 | 0.367 | 0.550 |
| 1c-18 | 0.335 | 0.057 |
| 1c-19 | 1.010 | 0.253 |
| 1c-20 | 0.090 | 0.030 |
| 1c-21 | 0.259 | 0.110 |

TABLE 2-continued

Cytotoxicity for A549 and SK-MEL-2 cells of the compound of formulae (1c)

| Com. No. | ED50(mg/mL) for A549 | ED50(mg/mL) for SK-MEL-2 |
|---|---|---|
| 1c-22 | 0.084 | 0.048 |
| 1c-23 | 0.085 | 0.041 |
| 1c-24 | >5 | >5 |
| 1c-25 | >5 | >5 |
| 1c-26 | 1.660 | 1.130 |
| 1c-27 | 0.870 | 0.347 |
| 1c-28 | 0.910 | 0.184 |
| 1c-29 | >5 | >5 |
| 1c-30 | 2.710 | 0.561 |
| 1c-31 | 0.119 | 0.035 |
| 1c-32 | 2.130 | 0.387 |
| 1c-33 | 0.258 | 0.062 |
| 1c-34 | 0.175 | 0.066 |
| 1c-35 | 0.014 | 0.015 |
| 1c-36 | 0.046 | 0.068 |
| 1c-37 | 0.019 | 0.070 |
| 1c-38 | 0.106 | 0.027 |
| Etoposide | 1.102 | — |

SK-MEL-2: Mouse skin cancer cell

TABLE 3a

Anti-cancer effect for mouse of organic acid ester of DDPT

| Com. No. | Dosage (mg/kg) | Time for administration | d12 TV | d12 SD | d12 IR | d13 TV | d13 SD | d13 IR |
|---|---|---|---|---|---|---|---|---|
| Etoposide | 36 | d1, d5, d9 | 0.62 | 0.19 | 62 | 0.76 | 0.26 | 68 |
| 1c-3 | 60 | d1 | 1.38 | 0.67 | 15 | 2.15 | 1.13 | 11 |
| 1c-4 | 60 | d1, d8 | 0.35 | 0.08 | 79 | 0.73 | 0.29 | 70 |
| 1c-5 | 60 | d1, d9 | 1.38 | 0.21 | 16 | 1.89 | 0.43 | 21 |
| 1c-6 | 60 | d1 | 1.04 | 0.15 | 36 | 1.79 | 0.91 | 25 |
| 1c-7 | 60 | d1 | 0.39 | 0.31 | 76 | 0.67 | 0.39 | 72 |
| 1c-8 | 60 | d1 | 0.99 | 0.96 | 39 | 1.33 | 0.60 | 45 |
| 1c-9 | 60 | d1 | 0.70 | 0.19 | 57 | 0.90 | 0.60 | 63 |
| 1c-10 | 60 | d1, d8 | 1.03 | 0.30 | 37 | 1.61 | 0.56 | 33 |
| 1c-11 | 60 | d1 | 0.64 | 0.24 | 61 | 1.02 | 0.48 | 57 |
| 1c-12 | 60 | d1, d8 | 1.08 | 0.09 | 34 | 1.53 | 0.43 | 36 |
| 1c-13 | 60 | d1, d5 | 0.99 | 0.29 | 39 | 1.45 | 0.15 | 40 |
| 1c-15 | 60 | d1, d5, d9 | 1.53 | 0.28 | 6 | 2.44 | 0.53 | −2 |
| 1c-24 | 60 | d1, d5, d9 | 1.51 | 0.43 | 8 | 2.13 | 0.82 | 11 |
| 1c-29 | 60 | d1, d5, d9 | 1.83 | 0.45 | −12 | 2.59 | 0.52 | −8 |
| Con | | | 1.63 | 0.11 | 0 | 2.40 | 0.35 | 0 |

TABLE 3b

Anti-cancer effect of unsaturated fatty acid(C-18) ester of DDPT

| Com. No. | Dosage (mg/kg) | Time for Administration | d12 TV | d12 SD | d12 IR | d13 TV | d13 SD | d13 IR |
|---|---|---|---|---|---|---|---|---|
| Etoposide | 36 | d1, d5, d9 | 0.29 | 0.09 | 77 | 0.61 | 0.14 | 75 |
| 1c-16 | 60 | d1, d5, d9 | 0.19 | 0.14 | 85 | 0.41 | 0.27 | 84 |
| 1c-17 | 60 | d1, d5, d9 | 0.12 | 0.04 | 90 | 0.26 | 0.01 | 89 |
| 1c-18 | 60 | d1, d5 | 0.11 | 0.08 | 91 | 0.25 | 0.04 | 90 |
| 1c-19 | 60 | d1, d5, d9 | 0.15 | 0.05 | 88 | 0.47 | 0.14 | 81 |
| 1c-20 | 45 | d1, d7 | 0.47 | 0.10 | 63 | 1.13 | 0.25 | 54 |
| 1c-21 | 60 | d1, d9 | 0.25 | 0.09 | 80 | 0.45 | 0.19 | 82 |
| 1c-22 | 60 | d1, d7 | 0.34 | 0.09 | 73 | 0.95 | 0.52 | 62 |
| 1c-23 | 60 | d1, d7 | 0.53 | 0.11 | 57 | 0.78 | 0.24 | 69 |
| Con | | | 1.24 | 0.50 | 0 | 2.48 | 1.16 | 0 |

TABLE 3c

Anti-cancer effect of unsaturated fatty acid(C-16, 20 or 22) ester of DDPT

| Com. No. | Dosage (mg/kg) | Time for Administration | d12 TV | d12 SD | d12 IR | d13 TV | d13 SD | d13 IR |
|---|---|---|---|---|---|---|---|---|
| Etoposide | 36 | d1, d5, d9 | 0.57 | 0.15 | 60 | 0.80 | 0.18 | 59 |
| 1c-14 | 60 | d1, d5 | 0.25 | 0.25 | 83 | 0.70 | 0.35 | 64 |
| 1c-25 | 60 | d1, d5, d9 | 0.53 | 0.34 | 63 | 0.75 | 0.25 | 62 |
| 1c-26 | 60 | d1, d5, d9 | 1.29 | 0.32 | 10 | 1.41 | 0.27 | 28 |
| 1c-27 | 60 | d1, d5, d9 | 0.24 | 0.16 | 83 | 0.44 | 0.13 | 77 |
| 1c-28 | 60 | d1, d5, d9 | 0.25 | 0.22 | 82 | 0.48 | 0.45 | 76 |
| 1c-30 | 60 | d1, d5, d9 | 1.28 | 0.25 | 11 | 1.67 | 0.63 | 15 |
| 1c-31 | 45 | d1, d5, d9 | 0.42 | 0.12 | 71 | 0.82 | 0.19 | 58 |
| Con | | | 1.44 | 0.30 | 0 | 1.96 | 0.30 | 0 |

TABLE 3d

Anti-cancer effect of dicarboxylic acid ester of DDPT

| Com. No. | Dosage (mg/kg) | Time for Administration | d12 TV | d12 SD | d12 IR | d13 TV | d13 SD | d13 IR |
|---|---|---|---|---|---|---|---|---|
| Etoposide | 36 | d1, d5, d9 | 0.34 | 0.04 | 78 | 0.43 | 0.06 | 84 |
| 1c-33 | 60 | d1, d5 | 0.77 | 0.07 | 51 | 1.32 | 0.45 | 50 |
| 1c-34 | 60 | d1, d5, d9 | 1.45 | 0.24 | 6 | 1.86 | 0.51 | 30 |
| 1c-35 | 60 | d1, d5, d9 | 1.30 | 0.28 | 17 | 1.70 | 0.24 | 36 |
| 1c-36 | 60 | d1, d5, d9 | 0.98 | 0.35 | 37 | 2.00 | 0.44 | 25 |
| 1c-37 | 60 | d1, d8 | 0.34 | 0.17 | 78 | 0.37 | 0.13 | 86 |
| 1c-38 | 60 | d1, d8 | 0.51 | 0.22 | 67 | 0.74 | 0.51 | 72 |
| Con | | | 1.55 | 0.33 | 0 | 2.66 | 1.09 | 0 |

Con: Dissolution Aid
d1~d13: lapsed Time from the Cancer Cell Transplanting
TV: Volume of Cancer ($mm^3$)
SD: Standard Deviation
IR: Inhibition Rate for Growth of Cancer (%)

As can be seen from the above results, the compound of the present invention generally shows a potent cytotoxicity for A549 and SK-MEL-2 cells.

Among the compounds of formulae (1a) and (1b), the compounds of 4'-demethyl-4'-O-alanoyl-(1a-1), 4'-demethyl-4'-O-leucinoyl-(1a-2), 4'-demethyl-4'-O-serinoyl-(1a-5), 4'-demethyl-4'-O-(2-hydroxyethyl)carbamoyl-(1b-5), 4'-demethyl-4'-O-(2-methoxyphenylcarbamoyl)-(1b-13), 4'-demethyl-4'-O-benzyl-carbamoyl-(1b-14), 4'-demethyl-4'-O-benzenesulfonylcarbamoyl-(1b-16), etc. exhibit a stronger cytotoxicity than DPT, and most of the compounds of formulae (1a) and (1b) were identified to have $ED_{50}$ values of 75~100 nM. Those of the compound of formula (1c) having 0.1 μg/ml or less of $ED_{50}$ value for A549 and SK-MEL-2 cells were calculated as 16 and 22, respectively, which were marked in italic and bold strokes in Table 2. Such a potent cytotoxicity means that the compound of the present invention may be utilized as a useful anti-cancer agent in the clinical area.

Further, Table 1 shows that the compounds of formulae (1a) and (1b) exhibit a higher inhibition rate (%) for the BDF1 mouse transplanted with Lewis Lung Cancer Cell (LLC) than the comparison compound of DPT (60%). Particularly, 4'-demethyl-4'-O-(2-leucinoyl)-(1a-2, 88%), 4'-demethyl-4'-O-(6-aminohexanoyl)-(1a-13, 85%), 4'-demethyl-4'-O-(isopropylcarbamoyl)-(1b-2, 90%) and 4'-demethyl-4'-O-(2-hydroxyethyl-carbamoyl)-1-deoxypodophyllotoxin (1b-5, 95.1%) represent the same degree of anticancer activity as Etoposide (90%), which is a currently used anti-cancer agent for the clinical purpose. In the case of the compounds wherein organic acid, unsaturated fatty acid or dicarboxylic acid is combined with DDPT through an ester bond (Table 3), 12 compounds among the total of 36 tested compounds show superior anti-cancer effects to Etoposide. Particularly, as can be seen from Tables 3b and 3c, most unsaturated fatty acid esters of DDPT exhibit better anti-cancer effects than Etoposide.

We cannot draw any relation between the chemical structure of the compound of the present invention and the anti-cancer activity from the above results. However, it is considered that the compound of the present invention shows a better anti-cancer acitvity than 4-demethyl-1-deoxypodophyllotoxin since the former has a higher bio-availability than the latter due to its improved water solubility. Particularly, the compounds having an unsaturated fatty acid in the molecule are expected to show the following advantages compared with the starting materials of DPT or DDPT. First, solubility may be increased due to the unsaturated group. This enables the compounds to overcome the demerit of DPT or DDPT that has a low water solubility and so, cannot be administered in excess. Second, since the compounds do not have methoxy or phenyl group, which is generally known to be easily excreted by the metabolic processes in the body, the retention time in the blood may be extended. Third, cancer cells which grow more rapidly than normal cells may absorb more quickly the essential fatty acid needed for cell growth from the extracellular region. During this process, the cancer cells may selectively absorb the relatively bulky materials having the essential fatty acid.

Experiment 4

Weight Change in the Period of Drug Administration

As an index of toxicity, the weight change during the period of drug administration was recorded for the compounds of formulae (1a) and (1b) compared with the comparison compound of Etoposide. As can be seen from the following Table 4, they show a similar behavior.

TABLE 4

Weight change(g) of mouse for 8 days from the cancer cell transplantation

| Day | 1 | 2 | 3 | 4 | 5 | 6 | 7 | 8 |
|---|---|---|---|---|---|---|---|---|
| Con. | 23 | 24 | 25.2 | 25.6 | 26 | 25.4 | 25.8 | 26 |
| 1a-2 | 23.3 | 24.3 | 25 | 26.1 | 26 | 25 | 25.3 | 26.1 |
| 1a-10 | 22.9 | 24.1 | 25 | 25.1 | 25.5 | 25.3 | 25 | 25.3 |
| 1a-11 | 22.8 | 24 | 24.2 | 25 | 24.4 | 25.4 | 25.4 | 25.5 |
| 1a-12 | 22.8 | 24.2 | 25 | 25.4 | 24.8 | 26 | 25.8 | 26.2 |
| 1a-13 | 23 | 24.2 | 25 | 25.2 | 25 | 25.5 | 26 | 26.2 |
| 1a-14 | 23 | 23.8 | 21.6 | 26 | 22.3 | 22.8 | 22.8 | 22.5 |
| 1b-2 | 22.8 | 23.6 | 23.2 | 25 | 25 | 26.1 | 26 | 26 |
| 1b-3 | 23.3 | 23 | 23.6 | 24.5 | 26 | 25 | 26 | 25.8 |
| 1b-4 | 23 | 23.9 | 25 | 26 | 25 | 26 | 26 | 25.5 |
| 1b-5 | 23.4 | 23.8 | 22.2 | 23.8 | 23.4 | 23.8 | 23 | 23.2 |
| DPT | 23.1 | 23.9 | 24 | 24 | 24.4 | 25 | 25 | 24.9 |
| Eto. | 23 | 24 | 25.1 | 26 | 25.9 | 26.3 | 25.6 | 26.6 | con.: Negative Control,
DPT.: Deoxypodophyllotoxin,
Eto: Positive Control (Etoposide, and
Day: Lapsed Days from the Cancer Cell Transplantation The above results show that the weight loss of about 0.5 g/mouse was observed in the case of Compound 1a-14 compared with the control group, and no weight loss was observed in the other cases. Therefore, it is highly possible that these compounds have no or extremely low toxicity to the body.

As explained above, the compound of the present invention generally has a similar or superior anti-cancer effect to the positive control, Etoposide, and thus, is expected to be a potent anti-cancer agent considering the aspect of dosage or formulation. That is, the compound of the present invention is cheap due to the easy synthesis, and has an advantage of being readily formulated due to the high solubility.

INDUSTRIAL APPLICABILITY

From the above results, it can be seen that the compound of formula (1) according to the present invention exhibits a potent anti-cancer activity. Particularly, it shows a strong cytotoxicity for the cancer cells of A549 and SK-MEL-2, and further a strong inhibition rate against the solid cancer which is induced by the transplantation of LLC cell into the hypodermic region of mouse. The compound of the present invention can be prepared by a relatively easy process and has a good solubility, and so can be applied to formulations such as injections with advantage.

What is claimed is:

1. A compound of the following formula (1):

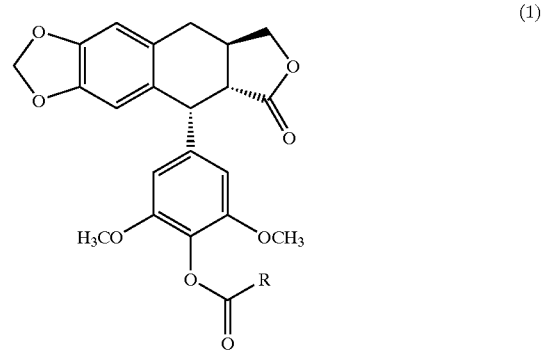

(1)

in which
R represents -A-$NH_2$; —NH—$R^1$; phenyl-$C_{2-4}$alkenyl unsubstituted or substituted by 1 to 5 $C_{1-4}$alkoxy; benzyl unsubstituted or substituted by amino or di$C_{1-4}$ alkylamino; straight-chain or branched $C_{1-21}$alkyl, $C_{15-21}$alkenyl, $C_{15-21}$alkadienyl, $C_{15-21}$alkatrienyl, $C_{15-21}$alkatetraenyl, or $C_{15-21}$alkahexaenyl; retinyl; or $C_{5-15}$carboxyalkyl, wherein
A represents amino acid residue, —$(CH_2)_{n1}$—; or —$(CH_2)_{n2}$—$C_6H_5$,
n1 denotes an integer of 2 to 8,
n2 denotes an integer of 1 to 4, and
$R^1$ represents straight-chain or branched $C_{1-4}$alkyl unsubstituted or substituted by substituent(s) selected from a group consisting of halogen and hydroxy; cycloalkyl; haloacetyl; allyl; phenyl unsubstituted or substituted by substituent(s) selected from a group consisting of halogen, $C_{1-4}$alkoxy, $C_{1-4}$alkyl and $C_{1-4}$alkylthio; benzyl; benzoyl; or benzenesulfonyl, or a geometric isomer thereof.

2. The compound of claim 1 which is selected from a group consisting of:
4'-demethyl-4'-O-alanoyl-1-deoxypodophyllotoxin;
4'-demethyl-4'-O-leucinoyl-1-deoxypodophyllotoxin;
4'-demethyl-4'-O-valinoyl-1-deoxypodophyllotoxin;
4'-demethyl-4'-O-glycinoyl-1-deoxypodophyllotoxin;
4'-demethyl-4'-O-serinoyl-1-deoxypodophyllotoxin;

4'-demethyl-4'-O-methionoyl-1-deoxypodophyllotoxin;
4'-demethyl-4'-O-phenylalanoyl-1-deoxypodophyllotoxin;
4'-demethyl-4'-O-threonoyl-1-deoxypodophyllotoxin;
4'-demethyl-4'-O-tyrosinoyl-1-deoxypodophyllotoxin;
4'-demethyl-4'-O-(3-aminopropanoyl)-1-deoxypodophyllotoxin;
4'-demethyl-4'-O-(4-aminobutanoyl)-1-deoxypodophyllotoxin;
4'-demethyl-4'-O-(5-aminopentanoyl)-1-deoxypodophyllotoxin;
4'-demethyl-4'-O-(6-aminohexanoyl)-1-deoxypodophyllotoxin;
4'-demethyl-4'-O-(7-aminoheptanoyl)-1-deoxypodophyllotoxin;
4'-demethyl-4'-O-(8-aminooctanoyl)-1-deoxypodophyllotoxin;
4'-demethyl-4'-O-(4-aminophenylacetyl)-1-deoxypodophyllotoxin;
4'-demethyl-4'-O-ethylcarbamoyl-1-deoxypodophyllotoxin;
4'-demethyl-4'-O-isopropylcarbamoyl-1-deoxypodophyllotoxin;
4'-demethyl-4'-O-2-chloroeylcarbamoyl)-1-deoxypodophyllotoxin;
4'-demethyl-4'-O-cyclohexylcarbamoyl-1-deoxypodophyllotoxin;
4'-demethyl-4'-O-(2-hydroxyethyl)carbamoyl-1-deoxypodophyllotoxin;
4'-demethyl-4'-O-chloroacetylcarbarmoyl-1-deoxypodophyllotoxin;
4'-demethyl-4'-O-allylcarbamoyl-1-deoxypodophyllotoxin;
4'-demethyl-4'-O-pheylcarbamoyl-1-deoxypodophyllotoxin;
4'-demethyl-4'-O-(4-fluorophenylcarbamoyl)-1-deoxypodophyllotoxin;
4'-demethyl-4'-O-(4-methoxyphenylcarbamoyl)-1-deoxypodophyllotoxin;
4'-demethyl-4'-O-(4-methylphenylcarbamoyl)-1-deoxypodophyllotoxin;
4'-demethyl-4'-O-(4-methylthiophenylcarbamoyl)-1-deoxypodophyllotoxin;
4'-demethyl-4'-O-(2-methoxyphenylcarbamoyl)-1-deoxypodophyllotoxin;
4'-demethyl-4'-O-benzylcarbamoyl-1-deoxypodophyllotoxin;
4'-demethyl-4'-O-benzoylcarbamoyl-1-deoxypodophyllotoxin;
4'-demethyl-4'-O-benzenesulfonylcarbamoyl-1-deoxypodophyllotoxin;
4'-demethyl-4'-O-(3,4,5-trimethoxyphenylcinnamoyl)-1-deoxypodophyllotoxin;
4'-demethyl-4'-O-(4-dimethylaminophenylacetyl)-1-deoxypodophyllotoxin;
4'-demethyl-4'-O-acetyl-1-deoxypodophyllotoxin;
4'-demethyl-4'-O-propanoyl-1-deoxypodophyllotoxin;
4'-demethyl-4'-O-butanoyl-1-deoxypodophyllotoxin;
4'-demethyl-4'-O-(3'-methylbutanoyl)-1-deoxypodophyllotoxin;
4'-demethyl-4'-O-heptanoyl-1-deoxypodophyllotoxin;
4'-demethyl-4'-O-octanoyl-1-deoxypodophyllotoxin;
4'-demethyl-4'-O-decanoyl-1-deoxypodophyllotoxin;
4'-demethyl-4'-O-benzoyl-1-deoxypodophyllotoxin;
4'-demethyl-4'-O-dodecanoyl-1-deoxypodophyllotoxin;
4'-demethyl-4'-O-tetradecanoyl-1-deoxypodophyllotoxin;
4'-demethyl-4'-O-hexadecanoyl-1-deoxypodophyllotoxin;
4'-demethyl-4'-O-(cis-9'-hexadecenoyl)-1-deoxypodophyllotoxin;
4'-demethyl-4'-O-octadecanoyl-1-deoxypodophyllotoxin;
4'-demethyl-4'-O-(cis-9'-octadecenoyl)-1-deoxypodophyllotoxin;
4'-demethyl-4'-O-(trans-9'-octadecenoyl)-1-deoxypodophyllotoxin;
4'-demethyl-4'-O-(cis-11'-octadecenoyl)-1-deoxypodophyllotoxin;
4'-demethyl-4'-O-(trans-11'-octadecenoyl)-1-deoxypodophyllotoxin;
4'-demethyl-4'-O-(cis,cis-9',12'-octadecadienoyl)-1-deoxypodophyllotoxin;
4'-demethyl-4'-O-(trans,trans-9',12'-octadecadienoyl)-1-deoxypodophyllotoxin;
4'-demethyl-4'-O-(cis-9',12',15'-octadecatrienoyl)-1-deoxypodophyllotoxin;
4'-demethyl-4'-O-(cis-6',9',12'-octadecatrienoyl)-1-deoxypodophyllotoxin;
4'-demethyl-4'-O-eicosanoyl-1-deoxypodophyllotoxin;
4'-demethyl-4'-O-(cis-11'-eicosenoyl)-1-deoxypodophyllotoxin;
4'-demethyl-4'-O-(trans-11'-eicosenoyl)-1-deoxypodophyllotoxin;
4'-demethyl-4'-O-(cis,cis-11',14'-eicosadienoyl)-1-deoxypodophyllotoxin;
4'-demethyl-4'-O-(cis-5',8',11',14'-eicosatetraenoyl)-1-deoxypodophyllotoxin;
4'-demethyl-4'-O-docosanoyl-1-deoxypodophyllotoxin;
4'-demethyl-4'-O-(cis-13'-docosenoyl)-1-deoxypodophyllotoxin;
4'-demethyl-4'-O-(cis-4',7',10',13',16',19'-docosahexaenoyl)-1-deoxypodophyllotoxin;
4'-demethyl-4'-O-retinoyl-1-deoxypodophyllotoxin;
4'-demethyl-4'-O-(5'-carboxy-pentanoyl)-1-deoxypodophyllotoxin;
4'-demethyl-4'-O-(7'-carboxy-heptanoyl)-1-deoxypodophyllotoxin;
4'-demethyl-4'-O-(9'-carboxy-nonanoyl)-1-deoxypodophyllotoxin;
4'-demethyl-4'-O-(11'-carboxy-undecanoyl)-1-deoxypodophyllotoxin;
4'-demethyl-4'-O-(13'-carboxy-tridecanoyl)-1-deoxypodophyllotoxin; and 4'-demethyl-4'-O-(15'-carboxy-pentadecanoyl)-1-deoxypodophyllotoxin.

3. A process for preparing the compound of formula (1) according to claim 1 characterized in that (1) DDPT of the following formula (3):

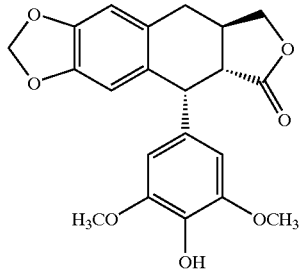

(3)

is esterified in an inert solvent and optionally in the presence of a condensing agent and an organic base with a compound of the following formula (4):

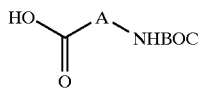

(4)

in which
A is defined as claim 1, and
BOC means t-butoxycarbonyl, to give a compound of the following formula (5):

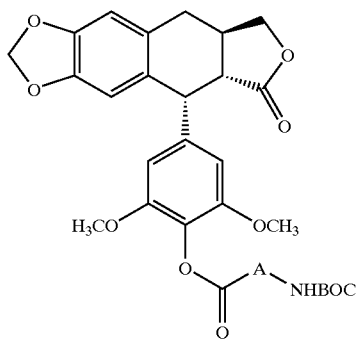

(5)

in which A and BOC are defined as above, which is then deprotected in the presence of an acid, a trialkylhalide, or a metal halide to give a compound of the following formula (1a):

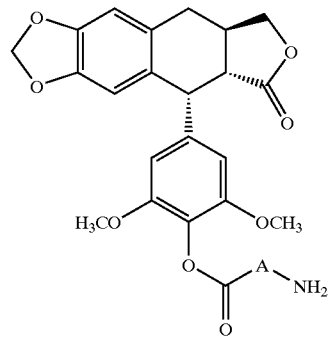

(1a)

in which A is defined as above; or (2) DDPT of formula (3) is reacted in an inert solvent and optionally in the presence of an organic base with a compound of the following formula (7):

$$R^1\text{—}N\text{=}C\text{=}O \quad (7)$$

in which $R^1$ is defined as claim 1, to give a compound of the following formula (1b):

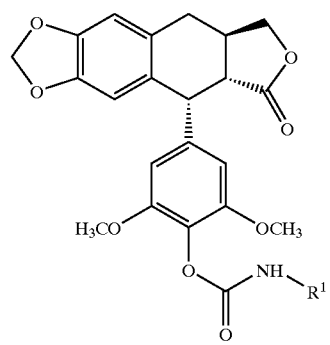

(1b)

in which $R^1$ is defined as above; or (3) DDPT of formula (3) is esterified in an inert solvent and optionally in the presence of a condensing agent and an organic base with a compound of the following formula (8):

$$R^2\text{—}COOH \quad (8)$$

in which $R^2$ represents phenyl-$C_{2-4}$alkenyl unsubstituted or substituted by 1 to 5 $C_{1-4}$alkoxy; benzyl unsubstituted or substituted by amino or di$C_{1-4}$ alkylamino; straight-chain or branched $C_{1-21}$alkyl, $C_{15-21}$ alkenyl, $C_{15-21}$alkadienyl, $C_{15-21}$alkatrienyl, $C_{15-21}$ alkatetraenyl, or $C_{15-21}$alkahexa-enyl; retinyl; or $C_{5-15}$carboxyalkyl, to give a compound of the following formula (1c):

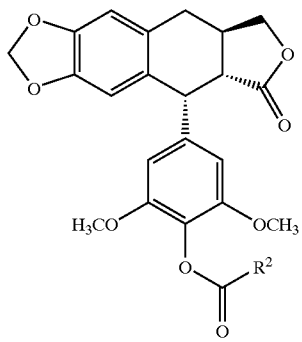

in which R² is defined as above.

4. The process of claim 3 wherein the solvent is haloalkane, and the organic base is amines or pyridines.

5. An anti-cancer composition comprising as an active ingredient the compound of formula (1) according to claim 1 together with pharmaceutically acceptable carriers.

6. A compound of the following formula (5):

in which
A is defined as claim 1, and
BOC means t-butoxycarbonyl.

* * * * *